(12) United States Patent
Nagy

(10) Patent No.: US 9,957,566 B2
(45) Date of Patent: May 1, 2018

(54) SCREENING METHOD

(75) Inventor: Zsuzsanna Nagy, Birmingham (GB)

(73) Assignee: THE UNIVERSITY OF BIRMINGHAM, West Midlands (GB)

( * ) Notice: Subject to any disclaimer, the term of this patent is extended or adjusted under 35 U.S.C. 154(b) by 533 days.

(21) Appl. No.: 13/384,272

(22) PCT Filed: Jul. 16, 2010

(86) PCT No.: PCT/GB2010/001365
§ 371 (c)(1),
(2), (4) Date: Jan. 16, 2012

(87) PCT Pub. No.: WO2011/007155
PCT Pub. Date: Jan. 20, 2011

(65) Prior Publication Data
US 2012/0115152 A1    May 10, 2012

(30) Foreign Application Priority Data
Jul. 16, 2009  (GB) .................................. 0912394.4

(51) Int. Cl.
*C12Q 1/68*  (2006.01)

(52) U.S. Cl.
CPC ...... *C12Q 1/6883* (2013.01); *C12Q 2600/118* (2013.01); *C12Q 2600/156* (2013.01); *G01N 2800/2821* (2013.01)

(58) Field of Classification Search
CPC ............ C12Q 1/6883; C12Q 2600/112; C12Q 2600/118; G01N 2800/2821; G01N 33/6896
See application file for complete search history.

(56) References Cited

U.S. PATENT DOCUMENTS 7,256,003 B2 *  8/2007  Iqbal .................. G01N 33/6896
435/7.1

FOREIGN PATENT DOCUMENTS

| WO | WO 1999/066075 | 12/1999 |
| WO | WO 2002/073212 | 9/2002 |
| WO | WO 2008/131367 | 10/2008 |

OTHER PUBLICATIONS

Cedazo-Minguez, A. J.Cell.Mol.Med.11(6):1227 (available Dec. 2007).*
Yan, H. et al. Applied Soft Computing 8:1105 (available Oct. 2007).*
Nuzzo, R. Biomedical Computation Review, Fall 2007, pp. 8-19.*
Ray, S. et al. Nature Medicine 13(11):1359 (available Oct. 2007).*
Prince, M.J. American Journal of Epidemiology 143(3):301 (1996).*
Nagy, Z., et al., "Cell Cycle Kinesis in Lymphocytes in the Diagnosis of Alzheimer's Disease," *Neuroscience Letters*, 317(2):81-84 (2002).
(Continued)

*Primary Examiner* — Diana B Johannsen
(74) *Attorney, Agent, or Firm* — Antoinette Giugliano; AGG Intellectual Property Law

(57) ABSTRACT

The present invention relates to clinical diagnosis of Alzheimer's disease or early-stage Alzheimer's disease in the live patient. In particular, the invention provides a screening method which can be used to assist with diagnosis of Alzheimer's disease in live human subjects, or to identify human subjects with a predisposition to Alzheimer's disease.

18 Claims, 13 Drawing Sheets

(56) References Cited

OTHER PUBLICATIONS

De Las Cuevas Natividad, et al., "Ca2+/calmodul in-dependant modulation of cell cycle elements pRb and P27kipl involved in the enhanced proliferation of lymphoblasts from patients with Alzheimer dementia," *Neurobiology of Disease,* 13(3):254-263 (2003).
Reiman, E, M, et al., "GAB2 alleles modify Alzheimer's risk in APOE .epsilon. 4 carriers," *Neuron,* 54(5):713-720 (2007).
Mayeux, R., "Biomarkers: Potential Uses and Limitations," *J. Am. Soc. for Experimental Neuro Therapeitics* (1):182-188 (2004).
Williamson, J, MS, et al., "Genetic Aspects of Alzheimer Disease," *Neurologist,* 15(2):80-86 (2009).
Cervilla, J., et al. "Premorbid cognitive testing predicts the onset of dementia and Alzheimer's disease better than and independently of APOE genotype," *J Neurol Neurosurg Psychiatry* 75:1100-1106 (2004).

\* cited by examiner

SCREENING METHOD

RELATED APPLICATIONS

This application is the U.S. National Phase of International Application No. PCT/GB2010/001365, filed Jul. 16, 2010, published in English, which claims priority under 35 U.S.C. § 119 or 365 to Great Britain Application No. 0912394.4, filed Jul. 16, 2009.

FIELD OF THE INVENTION

The present invention relates to clinical diagnosis of Alzheimer's disease or early-stage Alzheimer's disease in the live patient. In particular, the invention provides a screening method which can be used to assist with diagnosis of Alzheimer's disease in live human subjects, or to identify human subjects with a predisposition to Alzheimer's disease.

BACKGROUND TO THE INVENTION

As life expectancy increases, Alzheimer's disease (AD) is becoming a major health problem in the western world. There has been intensive research aimed at identifying a reliable cure or preventive measures for the disease, so far without success. One of the biggest problems in the design and testing of any therapeutic agent is the lack of clinical diagnostic criteria that could identify AD sufferers early enough for any meaningful intervention. The currently available clinical diagnostic tools do not allow a confident clinical diagnosis of Alzheimer's disease in other than severely demented patients.

Currently, there is no accepted "gold standard" diagnostic test for clinical diagnosis Alzheimer's disease in the live patient. The most often used clinical diagnostic criteria are the NINCDS/ADRDA criteria (McKhann, G. et al., (1984) Neurology 34: 939-944), originally designed for research purposes. These criteria are highly sensitive but have a low specificity. In this context, sensitivity is defined as the probability that the criteria will be satisfied in people who have Alzheimer's disease, and specificity is defined as the probability that the criteria will not be satisfied in people who do not have Alzheimer's disease. As a consequence of their low specificity, the NINCDS/ADRDA criteria are not ideal for clinical diagnostic purposes. Additionally they are not suitable as diagnostic criteria for clinical trials looking at preventive or curative therapies that may have their best chance of being effective if used before significant dementia has developed, since NINCDS/ADRDA require dementia in the patient as a criterion for an AD diagnosis.

A "confirmed" diagnosis of Alzheimer's disease can only be made post-mortem, by histological examination for the characteristic Alzheimer's disease pathology (accumulation of amyloid plaques and tangles), but this approach is clearly of no use for clinical diagnosis of AD in the living subject.

In recent years it has become more widely accepted that a pathogenic basis of Alzheimer's disease is the aberrant re-entry of different neuronal populations into the cell division cycle (Nagy Z, Esiri M M and Smith A D (1998) Neuroscience 84: 731 739). In healthy elderly individuals rapid cell cycle arrest and re-differentiation may follow this cell cycle re-entry. In contrast, in individuals with Alzheimer's disease the regulatory mechanisms appear to fail and the neurons progress into the late stages of the cell cycle leading to the accumulation of AD related pathology and/or neuronal death (Nagy Z, Esiri M M and Smith A D (1998) Neuroscience 84: 731 739). Several studies indicate that the cell cycle regulatory failure in Alzheimer's disease occurs at the G1/S transition checkpoint (see in particular Arendt T, Rodel L, Gartner U and Holzer M (1996) Neuroreport 7: 3047 9).

The appreciation that Alzheimer's disease can result from defective cell cycle regulation at the G1/S transition has led to the development of alternative approaches to AD diagnosis, based on detection of the underlying cell cycle regulatory defect rather than evaluation of outward symptoms of the disease, such as cognitive impairment (dementia). In this regard, International patent publication WO 02/073212 describes a diagnostic test, useful in the diagnosis of early-stage AD, which is based on screening for the presence of a cell cycle regulatory defect at the G1/S transition in non-neuronal cells of a test subject. The authors of WO 02/073212 found that the cell cycle regulatory defect at the G1/S transition previously seen in the neurons of Alzheimer's disease patients also occurs in non-neuronal cells, such as lymphocytes or fibroblasts, of AD patients. This in turn led to the development of a convenient blood test assay for the cell cycle regulatory defect which underlies (and precedes) the development of classic Alzheimer's disease symptoms, such as dementia (Zs Nagy, M Combrinck, M Budge, R McShane. Cell cycle kinesis in lymphocytes in the diagnosis of Alzheimer's disease. Neurosci Letters. 2002, 317, 2, 81-84.).

Apolipoprotein E (apoE) is an apolipoprotein essential for catabolism of triglyceride-rich lipoprotein constituents. The gene encoding apoE is polymorphic, with three major alleles ApoE2, ApoE3 and ApoE4, which translate into three major isoforms of the protein (apoE2, apoE3 and apoE4). The ApoE4 allele is a known genetic risk factor for AD in a variety of ethnic groups and can account for approximately 50% of cases in many populations (Waring S C and Rosenberg R N. Genome-Wide Association Studies in Alzheimer Disease. Arch Neurol 2008; 65(3):329-334). Individuals with either one or two copies of ApoE4 have a higher risk of developing AD, compared with carriers of the other isoforms. ApoE4 also reduces the median age of AD onset from 84 in non-carriers to 68 in homozygotes (Cedazo-Minguez A. Apolipoprotein E and Alzheimer's disease: molecular mechanisms and therapeutic opportunities. J. Cell. Mol. Med. 2007; 11(6): 1227-1238).

Although the ApoE4 allele is an established genetic risk factor for AD, this marker is not useful on its own for the diagnosis of AD in a clinical setting. Furthermore, it has not proven to be useful in combination with neuropsychological assessment of cognitive deficit in the clinical diagnosis of AD in subjects presenting with dementia (McConnell L M, Sanders G D, Owens D K. Evaluation of genetic tests: APOE genotyping for the diagnosis of Alzheimer disease. Genet Test 1999; 3(1):47-53).

SUMMARY OF THE INVENTION

The present inventors have now observed that the utility of the assay for defective cell cycle regulation at G1/S in non-neuronal cells (originally described in WO 02/073212) as in the diagnosis of Alzheimer's disease in the live subject can be improved by combining the assay result with apoE4 genotyping data from the same test subject in order to derive a new diagnostic criterion based on the combined result.

Therefore, in accordance with a first aspect of the invention there is provided a method of obtaining a diagnostic criterion associated with Alzheimer's disease in a human subject, which method comprises:

i) screening a human subject for the presence of a cell cycle regulatory defect at the G1/S phase transition in at least one non-neuronal cell,
ii) determining the apoE4 genotype of the same subject, and
iii) combining the result obtained in step ii) with the result obtained in step i), thereby obtaining a diagnostic criterion associated with Alzheimer's disease.

In one embodiment the results of step i) and step ii) are "combined" by entering the results as variables into a statistical algorithm (or diagnostic predictor) in order to derive a probability value, this probability value being a diagnostic criterion associated with Alzheimer's disease.

In accordance with a second aspect of the invention there is provided a method of improving the accuracy of a screen for the presence of a cell cycle regulatory defect associated with Alzheimer's disease, which method comprises:
i) screening the subject for the presence of a cell cycle regulatory defect at the G1/S phase transition in at least one non-neuronal cell,
ii) determining the apoE4 genotype of the same subject, and
iii) combining the result obtained in step ii) with the result obtained in step i), whereby the accuracy of the result obtained by combination is improved in comparison to the result obtained in step i).

In a related aspect the invention provides a method of improving the accuracy of diagnostic prediction based on a screen for the presence of a cell cycle regulatory associated with Alzheimer's disease, which method comprises:
i) screening the subject for the presence of a cell cycle regulatory defect at the G1/S phase transition in at least one non-neuronal cell,
ii) determining the apoE4 genotype of the same subject,
iii) combining the result obtained in step ii) with the result obtained in step i) and using the combined result for diagnostic prediction, whereby the accuracy of diagnostic prediction based on the result obtained by combination is improved in comparison to diagnostic prediction based on the result obtained in step i).

In accordance with a third aspect of the invention there is provided a method of assessing the risk of developing Alzheimer's disease in a human subject, which method comprises:
i) screening the subject for the presence of a cell cycle regulatory defect at the G1/S phase transition in at least one non-neuronal cell of the subject,
ii) determining the apoE4 genotype of the same subject, and
iii) combining the result obtained in step ii) with the result obtained in step i), and thereby assessing the risk of developing Alzheimer's disease in the human subject.

In one embodiment the results of step i) and step ii) are "combined" by entering the results as variables into a statistical algorithm (or diagnostic predictor) in order to derive a probability value for the test subject's risk of developing Alzheimer's disease.

In accordance with a fourth aspect of the invention there is provided a method to assist with clinical diagnosis of Alzheimer's disease in a live human subject, which method comprises:
i) screening the subject for the presence of a cell cycle regulatory defect at the G1/S phase transition in at least one non-neuronal cell of the subject,
ii) determining the apoE4 genotype of the same subject, and
iii) combining the result obtained in step ii) with the result obtained in step i).

In one embodiment the results of step i) and step ii) are "combined" by entering the results as variables into a statistical algorithm (or diagnostic predictor) in order to derive a probability value for the test subject having Alzheimer's disease.

In a further aspect, the invention provides a method to assist with diagnosis of pre-clinical Alzheimer's disease in a live human subject, which method comprises:
i) screening the subject for the presence of a cell cycle regulatory defect at the G1/S phase transition in at least one non-neuronal cell of the subject,
ii) determining the apoE4 genotype of the same subject, and
iii) combining the result obtained in step ii) with the result obtained in step i).

In a still further aspect the invention provides a method of obtaining a prognostic criterion indicative of the likely rate of cognitive decline due to Alzheimer's Disease in a human subject, which method comprises:
i) determining the presence of or the extent of a cell cycle regulatory defect at the G1/S phase transition in at least one non-neuronal cell of said subject,
ii) determining the apoE4 genotype of the same subject, and
iii) combining the result obtained in step ii) with the result obtained in step i), thereby obtaining a prognostic criterion indicative of the rate of cognitive decline due to Alzheimer's disease in said subject.

In non-limiting embodiments of each of the methods of the invention, step ii) may comprise screening the subject for the presence or absence of the apoE4 allele and thereby determining the number of apoE4 alleles carried by the test subject.

In all embodiments of the invention, the "combining" of step iii) typically involves statistical combination of the results obtained in the assays of step i) and step ii), as explained in detail herein.

DETAILED DESCRIPTION OF THE INVENTION

Figure 1:
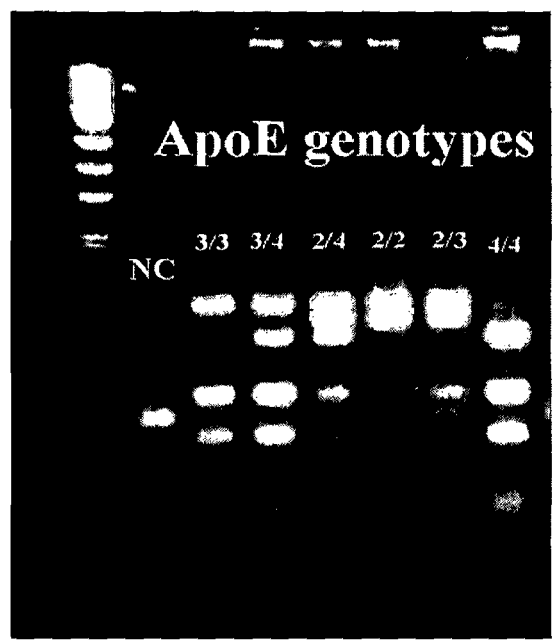
FIG. 1 shows the restriction fragment banding patterns characteristic of particular apoE genotypes.

In its various aspects, the invention relates to a "combination assay" in which the results of two independent assays; a first assay for the presence of a cell cycle regulatory defect at the G1/S phase transition in at least one non-neuronal cell of the subject under test, and a second assay in which the apoE4 genotype of the test subject is determined, are combined to generate a combined result which can then be used as a diagnostic criterion to assist with diagnosis of Alzheimer's disease, or as a prognostic criterion. In this context the term "diagnosis" is used in a very broad sense which encompasses clinical diagnosis of Alzheimer's disease in subjects who present with other symptoms consistent with Alzheimer's disease (such as dementia), including subjects who have been clinically diagnosed according to the NINCDS/ADRDA criteria, and also diagnosis of early stage or "pre-clinical" Alzheimer's disease in patients who do not meet the NINCDS/ADRDA criteria, and also prediction of the risk of developing AD in an asymptomatic subject or a subject exhibiting mild cognitive impairment. The clinical utility of the assay methodology of the invention is explained in further detail below.

The first assay, for the presence of a cell cycle regulatory defect at the G1/S phase transition in at least one non-neuronal cell of the subject, is known as a tool for diagnosis of Alzheimer's disease, particularly early diagnosis, as described in detail in WO 02/073212. By statistically combining the result of this assay with the results of apoE4 genotyping in the same subject, the overall accuracy of the result can be improved, when the diagnostic criterion obtained using the methodology of the invention is used in diagnosis.

In the following passages features of the invention will be described in further detail. It is to be understood that features described as being preferred or advantageous apply to all aspects of the invention unless stated to the contrary. Furthermore, any feature described as being preferred or advantageous may be combined with any other feature so-described, unless it is stated otherwise.

Step i)—Screening for the Cell Cycle Regulatory Defect in Non-Neuronal Cells

Screening for the existence of a cell cycle regulatory defect at the G1/S checkpoint in non-neuronal cells of a test subject may be carried out using the methodology described in WO 02/073212, the contents of which are incorporated herein in their entirety by reference, or by adaptations thereof, as described in the accompanying examples.

The assay is most preferably carried out in vitro on non-neuronal cells isolated from the human subject to be tested. The non-neuronal cells may be any non-neuronal cell type which exhibits the same cell cycle regulatory defect at the G1/S phase transition as is present in the neurons in Alzheimer's disease. In one embodiment the method is carried out on lymphocytes isolated from the subject and cultured in vitro. There are obvious practical advantages in being able to test for the presence of the cell cycle regulatory defect in a non-neuronal cell type. The use of lymphocytes is particularly convenient, since they are easily isolated from a blood sample and may be cultured in vitro. Another embodiment involves the use of fibroblasts, particularly skin fibroblasts which may be conveniently obtained from a skin biopsy. The sample of non-neuronal cells should typically not include cancer cells.

Cell-cycle defects can be identified in certain non-neuronal cancer cells. Thus, the diagnostic assays of the present invention are preferably to be conducted using non-cancerous non-neuronal cells, or using cells from patients that do not present clinical evidence of cancer (e.g., patients that do not exhibit tumors, cancer-specific antigens at concentrations associated with cancer), young patients (i.e., patients whose age does not correlate with AD (e.g., having an age at which fewer than 20%, more preferably fewer than 10%, still more preferably fewer than 5%, still more preferably fewer than 2%, still more preferably fewer than 1%, and most preferably fewer than 0.1% of the general population exhibit AD or an AD-related condition)). Since cancer is not typically associated with dementia or cognitive impairment, and AD and AD-related conditions are not typically associated with tumor antigen expression, tumorigenicity, those of ordinary skill in the art can readily perform a differential diagnosis between cancer and AD/AD-related conditions.

There are several ways in which to screen for the presence of a cell cycle regulatory defect at the G1/S phase transition in non neuronal cells, as described in detail in WO 02/073212. In one embodiment screening for the presence of the cell cycle regulatory defect may be accomplished by first inducing the cells to divide, then eliciting cell cycle arrest by addition of a cell division inhibitor substance and testing the responsiveness of the cells' G1/S cell cycle regulatory mechanisms to the addition of the cell division inhibitor substance.

The cell division inhibitor substance is typically a specific G1 inhibitor, with rapamycin being particularly preferred. Cell division may be induced by the addition of a mitogenic stimulus, for example one or more growth factors. If the test is carried out using lymphocytes then phytohaemagglutinin may be used to induce cell division.

The rationale is to first stimulate the cells to divide (e.g. with mitogenic stimulus), then attempt to arrest the cell cycle at the G1 stage using a cell division inhibitor (e.g. rapamycin or any other known G1 inhibitor) and then evaluate the effect of such treatment on the cell cycle regulatory system. The effect on cell cycle regulation may be evaluated by a variety of different means, as summarised below. The treatment with a cell division inhibitor may be referred to herein as "cell cycle inhibitory treatment" or "inhibitory treatment". If a cell cycle regulatory defect at the G1/S transition is present then this will affect the responsiveness of the cells to attempted cell cycle arrest. In general, the presence of a cell cycle regulatory defect at G1/S results in a reduced responsiveness to treatment with a cell division inhibitor, i.e. the inhibitory treatment is less effective in arresting the cell cycle at the G1/S checkpoint in cells with the cell cycle defect.

Various approaches may be implemented before and after the addition of the mitogenic stimulus and before and after the attempted arrest of the cell cycle to test the responsiveness of the cells to cell cycle inhibitory treatment (e.g. culture in the presence of rapamycin). A non-exhaustive list of preferred approaches which may be used in accordance with the invention is given below, other suitable approaches will be known to persons skilled in the art:

(1) Cell cycle analysis and calculation of the relative lengthening of the G1 phase of the cell cycle in cells from the subject as a result of exposure to a G1 inhibitor (e.g rapamycin). The relative lengthening of the G1 phase as a result of exposure to the cell division inhibitor may be calculated using the formula RL=100f−100 (expressed as a percent). "f" is the ratio of the time in G1 for cells (non-neuronal cells from the subject under test) exposed to inhibitory treatment with the cell division inhibitor or stimulus that induces cell cycle arrest (TG1tr) versus the time in G1 for untreated control cells (i.e. also non-neuronal cells from the subject under test) not exposed to inhibitory treatment (TG1c). f may be calculated according to the following relation:

$$f = TG1tr/TG1c = [In2\ In(2\ G1tr)][In(2\ G1c)]/[In(2\ G1tr)][In2\ In(2\ G1c)]$$

G1tr is the fraction of cells in G1 phase in the culture exposed to inhibitory treatment (e.g. cell division inhibitor)
G1c is the fraction of cells in G1 phase in a control cell from the same subject
(Darzynkiewicz Z (1993) In Fantes P and Brooks R (eds) The cell cycle. Oxford University Press, Oxford, pp 43 68)

Various techniques may be employed to obtain the values of TG1tr and TG1c. In one embodiment TG1tr and TG1c may be obtained by determining the proportion of cells in the various phases of the cell cycle for both treated cells (non-neuronal cells from the test subject treated with the G1 inhibitor) and untreated control cells (non-neuronal cells from the same subject not exposed to the G1 inhibitor). The proportion of cells in the various phases of the cell cycle may be readily determined by fluorescence activated cell sorting (FACS analysis) of suitably labelled cells, as described in the accompanying examples. In one embodiment, cells may be labelled (prior to FACS analysis) with an agent that is incorporated into DNA, e.g. propidium iodide or a nucleotide analogue. Cyclin A of S phase cells may also be labelled by immunocytochemistry.

The presence of a cell cycle regulatory defect at the G1/S phase transition is indicated by a reduced relative lengthening of the G1 phase in the presence of the G1 inhibitor, as compared to control cells not having a cell cycle regulatory defect at the G1/S phase transition. Suitable control cells include cells from an age-matched control subject. The control cells not having a cell cycle regulatory defect at the G1/S phase transition are not to be confused with the "untreated control" cells used for calculation of RL, which are cells from the test subject which have not been exposed to G1 inhibitor. As illustrated in the accompanying examples, the relative lengthening of TG1 induced by culture of dividing lymphocytes with rapamycin (TG1_Rapa) was significantly higher in control subjects than in Alzheimer's disease patients.

(2) Assessment of cell proliferation characteristics as an indicator of cell cycle arrest in cell cultures exposed to G1 inhibitor (e.g. rapamycin). In a typical screen proliferation characteristics are assessed for both cells treated with a G1 inhibitor, e.g. rapamycin, and untreated cells from the same subject. Since the inhibitory treatment will be effective only in the presence of an intact G1/S regulatory system, the difference in degree of proliferation between the treated and untreated cells will be significantly smaller in Alzheimer's disease patients (and subjects pre-disposed to AD) than in age matched control individuals. In other words, the G1 inhibitor (e.g. rapamycin) is less effective as an inhibitor of cell proliferation activity in cells having the G1/S regulatory defect (i.e. cells from AD patients and subjects pre-disposed to developing AD) than in control cells not having the G1/S defect.

The proliferation assay may be carried out according to any of the standard protocols known in the art. In one non-limiting embodiment, cell numbers in cultures of non-neuronal cells (e.g. lymphocytes) with or without G1 inhibitor (e.g. rapamycin) may be measured using a cytotoxicity assay. There are various commercial cytotoxicity assays suitable for this purpose, including lactate dehydrogenase (LDH) assays such as that used in the accompanying examples. The results of this assay may be used to calculate the number of cell divisions in culture with or without G1 inhibitor (n-n'), for both test subjects and normal controls. A preferred embodiment of the assay is based on culture of lymphocytes with and without rapamycin. The difference between the number of cell divisions in cultures with and without G1 inhibitor is one outcome measure of this assay. The inventors have observed that this result is diagnosis-dependent. The relative lengthening of cell division time in cultures treated with G1 inhibitor (rapamycin) versus untreated cultures is observed to be significantly lower in Alzheimer's disease subjects than in control subjects.

The above embodiment is non-limiting; the proliferation assay can be carried out using other known techniques, such as (for example) the MTT survival assay (commercially available from Chemicon International Ltd, see Mosmann, T. In J. Immunol. Methods, 1983, vol: 65, 55-63).

(3) Assessment of cell cycle regulatory protein or mRNA expression. Expression of cell cycle regulatory proteins may be assessed using standard techniques well known in the art such as, for example, immunoblotting, western blotting, ELISA or related methods. Assessment of expression of corresponding mRNAs encoding the cell cycle regulatory proteins may also be accomplished by means of standard methods such as, for example, hybridisation techniques, microarray analysis or related methods or amplification-based techniques such as RT-PCR or nucleic acid sequence-based amplification (NASBA). Suitable methods for the detection/quantitation of mRNAs which may be used in accordance to the invention will be well known to those skilled in the art. Certain of these methods, for example RT-PCR, rely on detection/quantitation of a cDNA copy of the relevant mRNA.

The cell cycle regulatory defect present in Alzheimer's disease may result in changes in the pattern of expression of cell cycle regulatory proteins, and their corresponding mRNAs. Screening for changes in expression of particular cell cycle regulatory proteins and/or the corresponding mRNAs may therefore be used to identify the presence (and determine the extent) of a cell cycle regulatory defect at G1/S. In addition, expression of cell cycle regulatory proteins may be used as a marker of progression through the cell cycle. Hence, the responsiveness of cells to inhibitory treatment may be assessed by looking at the expression of one or more cell cycle regulatory proteins, in order to determine the extent to which inhibitory treatment causes cell cycle arrest in cells from the test subject. Suitable cell cycle regulatory proteins include, but are not limited to, CDKN3, p15ink4B, p16ink4A, p19ink4D, p27kip1, p21cip1, p57kip2 and TP53. In addition, cyclin A and cyclin B expression may be used as biomarkers of S phase and G2 phase, respectively. In one particular embodiment, expression of cyclin A and/or cyclin B may be determined by ELISA. The sequences of all the above-listed proteins, and the genes encoding them, are publicly available. Antibodies useful in the detection of each of these proteins are available commercially.

(4) Assessment of cell viability and cell death by any method known in the art. When a proliferating cell is arrested in the G1/S transition one of two possible "downstream" phenomena may result, either differentiation or programmed cell death. These downstream phenomena may be used as an indication of the presence in a cell population of a regulatory defect at the G1/S transition, since if regulation of the G1/S transition is defective then the downstream effects of cell cycle arrest at G1/S will also be abnormal. A lower degree of cell death or higher degree of cell viability in response to inhibitory treatment in cells from the test subject, as compared to control cells, is taken as an indication of defective regulation at G1/S.

(5) Assessment of cell death-related (inducing or preventing) protein or mRNA expression using standard techniques. In this embodiment, expression of cell death-related proteins, or the corresponding mRNAs, is used as an indirect assessment of the downstream effects of treatment with a cell division inhibitor inducing cell cycle arrest at the G1/S transition. Suitable cell death-related proteins include members of the bcl-2 family of proteins, of which there are many known in the art.

(6) Assessment of the DNA content of the non-neuronal cells, with or without cell cycle analysis. In this embodiment, measurement of the DNA content of cells from the test subject treated with a cell division inhibitor provides an indirect indication of the presence of a regulatory defect at the G1/S transition in such cells. The rationale behind this method is the difference in DNA content between cells in the G1 phase and cells in the G2 phase which have passed through the DNA replication stage of the cell cycle. When a population of normal cells (i.e. without a regulatory defect at G1/S) are treated to induce cell cycle arrest in G1 or at G1/S, the majority of the cells will remain in the G1 phase. However, if cells have a regulatory defect at G1/S, a proportion of the cells will pass through the G1/S checkpoint and undergo DNA replication. Thus an increased DNA content in cells from a test subject, as compared to control cells not having a regulatory defect at G1/S, following treatment to induce cell cycle arrest at G1 is taken as an indication of the presence of a regulatory defect at G1/S.

The above list of techniques suitable for use in testing the responsiveness of non-neuronal cells, particularly cultured lymphocytes, to inhibitory treatment with a cell division inhibitor is intended to be illustrative of rather than limiting to the invention. Other suitable techniques are described in WO 02/073212.

The results of different assays for the cell cycle regulatory defect at G1/S may be statistically combined for the purposes of diagnostic prediction, in order to derive a measure of the risk or "odds" that subjects with a particular test result will develop Alzheimer's disease (or not). Statistically analysis, for example logistic regression, may be used to assess the relative contributions of the variables which contribute significantly to diagnosis (e.g. AD versus control) or to prediction of risk of developing AD, and to combine the results of two different assay methodologies in order to derive a diagnostic predictor for calculation of the odds that a subject will (or will not) develop AD with a particular set of test results. Suitable "combinations" of assay results (variables) include, but are not limited to, difference between the number of cell divisions in cultures with or without G1 inhibitor (e.g. lymphocytes cultured with or without rapamycin) (variable n-n') combined with relative lengthening of TG1 under G1 inhibitor (e.g. lymphocytes cultured with or without rapamycin) (co-variable TG1_Rapa), as illustrated in the examples.

Step ii)—apoE4 Genotyping

The molecular nature of the apoE genetic polymorphism is well characterised (see OMIM database accession 107741 and references cited therein). Briefly, apolipoprotein E exists in three major isoforms (apoE2, apoE3 and apoE4), which are coded for by three alleles (epsilon 2, 3 and 4). All six possible pairings of the three alleles can occur in human subjects, i.e. 2/2, 2/3, 2/4, 3/3, 3/4 and 4/4. Methods for apoE genotyping are generally known in the art. In a non-limiting embodiment, illustrated in the accompanying examples, genomic DNA may be prepared from cells of the test subject (e.g. PBLs) using standard DNA purification techniques. The apoE genotype of the subject may then be determined by PCR-RFLP, as described in the accompanying examples, or by any other suitable genotyping methodology. The genotyping methodology is not itself material to the invention, since the genotype of the test subject is absolute, and not altered by any particular genotyping method.

The invention thus includes determining the apoE genotype of the subject. As used herein, such act of determining includes both the de novo apoE genotyping of a subject having a previously undetermined genotype as well as the consideration and use of previously determined apoE genotype data of such subject.

In all embodiments of the method of the invention, the number of apoE4 alleles present in the test subject may be used as a co-variable for the purposes of the statistical combination with the result of the assay for the regulatory defect at G1/S (test i). In such embodiments the chosen genotyping method should, at least, allow one to determine the number of apoE4 alleles present in the test subject. Whilst the genotype of any given test individual is fixed, when considering a population of test and control subjects to be screened, the number of apoE4 alleles present in each individual (0, 1 or 2) may be treated as a variable for the purpose of statistical analysis.

Statistical Combination

In order to achieve the full benefit and advantage of the invention, the assay result (or outcome measure) of step i) must be combined with the genotyping result obtained in step ii).

In all the methods of the invention, the results of step i) and step ii) may be "combined" in order to derive a probability value for a particular outcome/diagnostic or prognostic prediction. For any given test subject, the probability value may be calculated by entering the results of step i) and step ii) as variables into a statistical algorithm. The algorithm to be used for calculation of the probability value can itself by derived by applying the assays of step i) and step ii) to a population of test (i.e. AD) and control (non-AD) subjects and then statistically combining the results in order to determine the contribution of the two (independently assayed) test results to diagnostic (or prognostic) prediction (e.g. AD versus control). This can be achieved by treating the result of step i) (e.g. RL, TG1_Rapa, n-n' or any statistical combination thereof) as a first variable, and the apoE4 genotype (e.g. number of apoE4 alleles) as a co-variable, as illustrated in the accompanying examples. Standard statistical analysis methods can be used for this purpose, for example logistic regression. The present inventor has observed that when the two (independently obtained) assay results are combined in this manner, the overall accuracy of the result obtained by combining the result of step i) and the result of step ii) as a biomarker of clinical outcome (e.g. as a predictor of risk of developing AD) is increased, relative to the assay of step i) alone or of step ii) alone. The resulting "combined" assay also exhibits high clinical specificity (typically greater than 90%) and sensitivity (typically greater than 65%).

The "result" of the assay for the cell cycle regulatory defect at G1/S (step i) to be combined with apoE4 genotype (step ii) may itself be a "combined" result. As explained above, the results of two different assays which indicate the presence of the cell cycle regulatory defect at G1/S may be combined (e.g. by logistic regression) for the purposes of predicting risk (odds) of developing Alzheimer's disease. According to the invention, this combined result may itself be treated as a variable and combined (for example by logistic regression) with the co-variable of apoE genotype (specifically number of apoE4 alleles) in order to derive a diagnostic prediction.

Although logistic regression is the preferred approach for statistical combination of the test results, other statistical techniques may be used, including for example ANOVA, Levene's test, student Newman-Keuls test, Chi-square test, etc.

Once the diagnostic predictor, i.e. the algorithm for calculation of odds based on the results of independent assays for the G1/S defect and the apoE genotype, has been derived (e.g. by logistic regression), ROC (receiver operating characteristic) analysis may be used in order to establish a cut-off point at which test subjects are classified as "AD" (or "probable AD") or "not AD" (or "probable not AD") based on the combination of the two independent assay results (i.e. the calculation of odds). This cut-off value may be applied in order to give a binary read-out, ie. "AD" or "not AD" for classification of patient samples.

It is noteworthy that ApoE4 genotyping has been shown to be ineffective for the clinical diagnosis AD on its own or in combination with assessment of cognitive deficit. However, the present inventor found that combination of ApoE4 genotyping with the assay for defective cell cycle regulation at G1/S unexpectedly increased the number of patients correctly diagnosed when the result of the combined assay was used for diagnostic prediction, as compared to the numbers correctly diagnosed when using the result of step i) alone for diagnostic prediction.

Clinical Utility of the Assay

The method of the invention is used to derive a diagnostic criterion by combination of the results of two independent assays. One of these assays detects the presence of a cell cycle regulatory defect at the G1/S transition in non-neuronal cells of a human test subject. This cell cycle defect has been described previously in the literature, and is indeed known to be associated with risk of developing Alzheimer's disease. However, the clinical reliability and usefulness of diagnostic prediction based on the combined result of the G1/S cell cycle defect assay plus apoE4 genotyping is improved, as compared to diagnostic prediction based on the result of the assay for the G1/S defect alone. In this regard it should be noted that the apoE4 genotype is not itself used in the invention as a predictor of clinical outcome (e.g. as a "risk factor", for AD), rather the apoE4 genotyping result is combined with the result obtained when assaying for the G1/S cell cycle regulatory defect in order to obtain a combined result which may then be used as a diagnostic criterion (i.e. a basis for diagnostic prediction). In fact, the present inventor has observed that the outcome of the assay for the cell cycle regulatory defect (step i) is not dependent on underlying apoE4 genotype, hence the two assay results are technically (and biologically) independent of one another. Yet, when the results of the two (independent) assays are combined, the resulting diagnostic criterion performs better (in diagnostic prediction) than the result of either assay used alone.

In the various aspects of the invention, the basic methodology of:
i) screening the subject for the presence of (or extent of) a cell cycle regulatory defect at the G1/S phase transition in at least one non-neuronal cell of the subject,
ii) determining the apoE4 genotype of the same subject, and
iii) statistically combining the result obtained in step ii) with the result obtained in step i) can be used in a variety of different clinical applications.

In certain embodiments, the basic methodology may be used to assess risk of developing Alzheimer's disease, or to detect very early onset AD, prior to emergence of "classical" AD symptoms, particularly dementia.

Alzheimer's disease is traditionally defined as a progressive, degenerative disease of the brain which results in dementia. Hence, the predominant outward symptom of AD is dementia, however not all patients presenting with dementia have Alzheimer's disease. Although Alzheimer's disease is know to be the major cause of dementia (particularly in subjects over 65 years), there are several alternative causes. AD can be differentiated from other dementias by the presence of the characteristic pathology of amyloid plaques and tangles.

The present inventor postulates that Alzheimer's disease should, in fact, be viewed as a disease caused by defective cell cycle regulation, and specifically defective regulation at the G1/S checkpoint. Without wishing to be bound by theory, the inventor is of the opinion that the defect in neurons is causative of Alzheimer's disease pathology (i.e. accumulation of amyloid) and symptoms, such as dementia. An equivalent defect in cell cycle regulation is also detectable in non-neuronal cells (e.g. lymphocytes), providing the basis for the assays of the present invention.

Since the cell cycle regulatory defect is causative, and will hence precede development of recognisable clinical symptoms of AD (such as dementia), the assay methodology of the invention, which gives an improved diagnostic prediction relative to diagnostic prediction based on assessment of the G1/S cell cycle defect alone, will find major clinical utility in assessing risk of developing AD. In other words, the assay methodology of the invention can identify subjects who are predisposed to develop AD due the presence of the underlying cell cycle regulatory defect, irrespective of the presenting symptoms of that patient.

In certain embodiments, the methodology of the invention may be used to screen asymptomatic subjects to assess risk/predisposition for developing full blown AD symptoms, due to the presence of the cell cycle regulatory defect. In other embodiments the same basic methodology may be used to screen subjects who are "symptomatic", to varying degrees. In certain embodiments the methodology of the invention may be applied to human subjects who already meet the NINCDS/ADRDA criteria, in which case the methodology of the invention may provide an additional diagnostic criterion which is independent of neuropsychological symptoms (i.e. is not based on assessment of cognitive function). The additional diagnostic criterion provided by the methodology of the invention may therefore provide a useful adjunct to NINCDS/ADRDA, to assist clinical diagnosis in the live patient.

In other embodiments, the methodology of the invention may be applied to human subjects to whom the NINCDS/ADRDA has not been applied, or to human subjects who do not meet the NINCDS/ADRDA criteria. In this regard the methodology of the invention could be viewed as providing an alternative basis for clinical diagnosis of Alzheimer's disease in the live patient (or at least for identification of subjects who are very likely AD) which is independent of the NINCDS/ADRDA criteria.

In a particularly important embodiment, the basic methodology may be used to screen subjects presenting with mild cognitive impairment (MCI) in order to identify those at risk/predisposed to developing full-blown AD symptoms (i.e. dementia), or even those subjects who could be considered as being in the "early" stages of AD (whether this be defined by classical symptoms, or presence of characteristic pathology, i.e. amyloid accumulation in the brain). The present inventor has shown in a longitudinal study that MCI patients who additionally show a positive screening result for the cell cycle regulatory defect at G1/S in non-neuronal cells exhibit first signs of cognitive decline on average 10 years earlier than MCI subjects who do not exhibit the cell cycle regulatory defect. Hence, presence of the cell cycle defect is predictive of "risk" that MCI patients will go on to develop cognitive deficit.

In other embodiments, it could be considered that the same basic methodology is being applied "diagnostically", or at least to assist in clinical diagnosis of AD in the live patient. In such embodiments, the test subject may be a human subject presenting with symptoms generally associated (although not necessarily exclusively) with AD. A typical example would be patients presenting with symptoms of cognitive deficit/cognitive decline or dementia. In this patient population, the basic methodology of the assay of the invention could be used to substantiate that a patient presenting with symptoms of cognitive impairment/dementia actually has the underlying cell cycle regulatory defect associated with AD, and hence confirm that the dementia is symptomatic of AD, and not some other disease. Other presenting "symptoms" of AD might include changes in brain structure visible using imaging techniques, such as MRI. In clinical practice, the diagnostic criterion obtained using the assay methodology of the invention will provide a valuable additional tool to assist with all aspects of the diagnosis of AD in living patients, either alone or in combination with other diagnostic tests for AD symptoms.

The availability of an accurate test for the cell cycle regulatory defect underlying the pathology of Alzheimer's disease significantly improves the ability to diagnose the condition, and in particular enables early diagnosis. It is apparent from the work of the present inventor that a defect in cell cycle control is detectable in peripheral (non-neuronal) cells, such as lymphocytes, well before the clinical signs of fully developed dementia appear. Hence, the method of the invention provides a tool for early diagnosis of Alzheimer's disease, especially detection of individuals who are in pre-clinical stages of the disease, and for identification of individuals who have not yet developed Alzheimer's disease as such but are "at risk" of doing so because of the presence of the cell cycle regulatory defect.

Additionally, the availability of an accurate test for the cell cycle regulatory defect underlying the pathology of Alzheimer's disease significantly improves the ability to determine the therapeutic efficacy of a therapy (or the potential therapeutic efficacy of a candidate therapy) for the treatment of Alzheimer's disease in a human subject recipient of such therapy. Such therapy or candidate therapy can include an administered medicament, procedure, or regimen. Thus, for example, a non-neuronal cell of a subject recipient of an Alzheimer's disease therapy or candidate therapy is evaluated to determine the extent of a cell cycle regulatory defect at the G1/S phase transition. The extent of the determined cell cycle regulatory defect at the G1/S phase transition is evaluated in light of the subjects apoE4 genotype to thereby determine the therapeutic efficacy of the therapy or potential therapy for the treatment of Alzheimer's disease in such subject.

The present inventors have further observed that the rate of cognitive decline on the 30-point Mini-Mental State Examination (MMSE) is significantly accelerated in probable Alzheimer's disease patients who exhibit a cell cycle regulatory defect at the G1/S phase transition in non-neuronal cells (i.e. a "positive" result in the assay of step (i)), and is also significantly accelerated in probable Alzheimer's disease patients who test positive for the presence of one or more ApoE4 alleles. Moreover, the association with accelerated cognitive decline is significantly strengthened when the results of both assays are statistically combined to derive a prognostic criterion.

Accordingly, in a further aspect of the present invention there is provided a method of obtaining a prognostic criterion indicative of the likely rate of cognitive decline due to Alzheimer's Disease in a human subject, which method comprises:

i) determining the presence of or the extent of a cell cycle regulatory defect at the G1/S phase transition in at least one non-neuronal cell of said subject, ii) determining the apoE4 genotype of the same subject, and iii) combining the result obtained in step ii) with the result obtained in step i), thereby obtaining a prognostic criterion indicative of the likely rate of cognitive decline due to Alzheimer's disease in said subject.

This method may be applied to human subjects presenting with probable AD, or to subjects with dementia of the Alzheimer type, including but not limiting to subjects with a clinical diagnosis of AD based on the NINCDS/ADRDA criteria, in order to predict the likely rate of cognitive decline in said subject during the course of their disease.

It will be clear to those of skill in the art that the particular embodiments described with respect to the previous aspects of the invention apply equally to this further aspect.

The scope of the present invention also extends to the following methods in which the "combining" step is applied to previously obtained results from the assay of step i) and the assay of step ii):

A method of obtaining a diagnostic criterion associated with Alzheimer's disease in a human subject, which method comprises:
combining the result obtained in an assay in which a human subject is screened for the presence of a cell cycle regulatory defect at the G1/S phase transition in at least one non-neuronal cell with the result obtained by apoE4 genotyping of the same subject, and thereby obtaining a diagnostic criterion associated with Alzheimer's disease A method of improving the accuracy of a screen for the presence of a cell cycle regulatory defect associated with Alzheimer's disease, which method comprises: combining the result obtained in an assay in which a human subject is screened for the presence of a cell cycle regulatory defect at the G1/S phase transition in at least one non-neuronal cell with the result obtained by apoE4 genotyping of the same subject, whereby the accuracy of the combined result is improved in comparison to the result obtained in the assay for the cell cycle regulatory defect alone.

A method of assessing the risk of developing Alzheimer's disease in a human subject, which method comprises: combining the result obtained in an assay in which a human subject is screened for the presence of a cell cycle regulatory defect at the G1/S phase transition in at least one non-neuronal cell with the result obtained by apoE4 genotyping of the same subject, and thereby assessing the risk of developing Alzheimer's disease.

A method to assist with clinical diagnosis of Alzheimer's disease in a live human subject, which method comprises: combining the result obtained in an assay in which a human subject is screened for the presence of a cell cycle regulatory defect at the G1/S phase transition in at least one non-neuronal cell with the result obtained by apoE4 genotyping of the same subject.

A method for assessing the efficacy of a candidate therapy for the treatment of Alzheimer's disease in a human subject recipient of such therapy, which method comprises: combining the result obtained in an assay in which a human subject is screened for the presence of a cell cycle regulatory defect at the G1/S phase transition in at least one non-neuronal cell with the result obtained by apoE4 genotyping of the same subject, thereby obtaining a diagnostic criterion associated with the efficacy of said candidate therapy for the treatment of Alzheimer's disease.

A method of obtaining a prognostic criterion indicative of the likely rate of cognitive decline due to Alzheimer's Disease in a human subject, which method comprises: combining the result obtained in an assay in which a human subject is screened for the presence of a cell cycle regulatory defect at the G1/S phase transition in at least one non-neuronal cell with the result obtained by apoE4 genotyping of the same subject, thereby obtaining a prognostic criterion indicative of the rate of cognitive decline due to Alzheimer's disease in said subject.

The invention will be further understood with reference to the following experimental examples.

Example 1

The following method illustrates testing of a test population of clinically diagnosed Alzheimer's patients (AD) and patients with mild cognitive impairment (MCI), plus age-matched control subjects, using a method according to the invention.

Test Subjects

For the "clinically diagnosed" Alzheimer's cases, AD was diagnosed using the NINCDS criteria. The control subjects were accepted as control if they presented no cognitive impairment for several years running. Mild cognitive impairment (MCI) was diagnosed using standard neuropsychological criteria.

Step i)—Screening for Cell Cycle Regulatory Defect at G1/S in Non-Neuronal Cells The following methodology was used to assess cell cycle regulation at G1/S in preparations of peripheral lymphocytes prepared from test subjects and control subjects.

1) Sample Collection and Lymphocyte Separation

Samples of venous blood (approx 5-10 ml) were taken from human subjects in heparinised vacutainers. Samples were stored/transported at room temperature for a maximum of 36-48 hours after recovery.

Peripheral lymphocytes were separated using Lymphoprep™ (Axis Shield UK), according to the manufacturer's instructions. Once separated, lymphocytes were stored (as appropriate) in 90% fetal calf serum (FCS, heat inactivated) plus 10% DMSO at −80° C. Storage at −80° C. is suitable for a period of a few months, but for longer term storage samples should be placed in liquid nitrogen.

2) Cell Culture with or without G1 Inhibitor (Rapamycin)

Peripheral lymphocytes (thawed from storage as appropriate) were cultured in a growth medium of RPMI 1640 supplemented with 15% FCS (heat inactivated), plus 2% I-glutamine and 1% penicillin/streptamycin, in the presence of 2.5% phytohaemagglutinin (PHA) for 48 hours at 37° C., 5% $CO_2$, to reach exponential growth. Cultures were prepared in a 96 well plate format, with 6 or 8 wells allocated to each patient (test subject). One single plate could therefore hold eleven sets of patient samples, plus one set of standard samples.

Once exponential growth of the cells was achieved, the lymphocyte cultures were treated with either growth medium (as above) alone, or the same growth medium plus 100 ng/ml rapamycin, in triplicate/quadruplicate for each patient.

Cell cultures were harvested after 24 hours. Samples intended for cytotoxicity testing (LDH assay) were frozen at −20° C., whereas samples intended for analysis by flow cytometry were fixed in 85% cold ethanol.

3) LDH Cytotoxicity Assay

Measurement of cell numbers in the cell cultures prepared in 3) was carried out by LDH cytotoxicity assay using the CytoTox 96® Non-Radioactive Cytotoxicity Assay Kit from Promega, according to the instructions supplied by the manufacturer.

The assays were set up in 96-well plate format, using 30 µl of lymphocyte culture and 50 µl of LDH substrate mix per well (substrate mix is a component of the CytoTox kit, diluted prior to use). Patient samples cultured with or without rapamycin were each tested in triplicate. The assay plates also included diluted standards of LDH positive control (serial dilutions of LDH positive control in lymphocyte culture medium; triplicate samples of 30 µl at each of 1:2500, 1:5000, 1:10,000, 1:20,000, 1:40,000, 1:80,000 and 1:160,000 dilution), to allow construction of a calibration curve.

After addition of the substrate mix to the patient samples and calibration samples, the assay plates were incubated at RT in the dark for 15-30 minutes, continually observing the colour change to ensure that the calibration curve stays linear and that master samples colour intensity does not exceed the calibration curve. The reactions were then stopped by adding 50 µl of cold Stop Solution (component of the CytoTox kit) to each well. Optical density was then read at 490 nm.

4) Flow Cytometry and Cell Cycle Analysis 96-well plate lymphocytes cultures (with or without rapamycin) fixed in ethanol (end of step 3) were spun at 400 g for 10 minutes at RT with no breaks. Supernatants were removed and the cell pellets resuspended in 0.300 ml ice-cold PBS/well. The plates were spun again at 400 g for 10 minutes at RT with no breaks. Supernatants were again removed and the cell pellets re-suspended in 0.080 ml of propidium iodide (P1) staining solution/well.

PI staining solution was prepared as follows:
To 10 ml of PBS (Ca and Mg free, tissue culture grade, from Sigma) add:

200 microL of PI stock solution (1 mg/ml)
100 microL RNAse A solution (10 mg/ml)
10 microL of Triton X
Mix well and keep protected from light throughout.

The flow cytometer (FacsCalibur BD) was set up to distinguish well between the G1 and G2 peaks (at least 200 units apart).

The interpretation of cell cycle phases was based on the recommendations of M G Ormerod (Flow Cytometry, 3rd edition, p 95).

Using as a Marker measure the PI reading equivalent to the G1 peak and the G2 peak the parameter X was calculated based on the relation:

$$X = (G2\text{peak} - G1\text{peak})/4$$

Based on these measurements the following markers were set up:
G1 cells: (G1peak−X) to (G1peak+X)
S cell: (G1 peak+X) to (G2peak−X)
G2 cells: (G2peak−X) to (G2peak+X)
Apoptosis marker: anything below (G1 peak−X)
All dividing cells: (G1 peak−X) to (G2peak+X)

From these measurements the cell population densities were calculated as follows:
S phase population: S cells/all dividing cells within LC-UC marker)
G1 phase population: G1 cells/(all dividing cells)
G2 phase population: G2 cells/(all dividing cells)

5) Analysis of Results

The LDH cytotoxicity assay gave a value for total cell numbers in each lymphocyte culture (with or without rapamycin). From the cell numbers data, it was possible to derive figures for the number of cell divisions (n) and population doubling time (PDT). The cell population densities obtained by analysis of the FACS data, plus the PDT result were then used to calculate the parameter TG1 (relative lengthening of the G1 phase). This can be done using the following equation:

$$T_{G1} = PDT \frac{\ln 2 - \ln(2 - f_{G1})}{\ln 2}$$

$f_{G1}$ is the proportion of cells in the G1 phase of the cell cycle as measured by flow cytometry.

Finally, TG1 values calculated for rapamycin treated and untreated lymphocyte cultures from the same test subject were compared.

Logistic regression can be used to combine the variables n-n' and TG1_Rapa in order to derive an odds value for diagnostic prediction, as shown in Table 1.

TABLE 1 logistic regression, results of lymphocyte culture assay

| Logistic regression | |
| --- | --- |
| Dependent Y | DG_ROC |
| Method | Backward |
| Enter variable if P< | 0.05 |
| Remove variable if P> | 0.1 |
| Sample size | 69 |
| Cases with Y = 0 | 43 (62.32%) |
| Cases with Y = 1 | 26 (37.68%) |

TABLE 1-continued logistic regression, results of lymphocyte culture assay

Table 1.1—Overall Model Fit

| | |
| --- | --- |
| Null model −2 Log Likelihood | 91.42247 |
| Full model −2 Log Likelihood | 66.73814 |
| Chi-square | 24.6843 |
| DF | 2 |
| Significance level | P < 0.0001 |

Table 1.2—Coefficients and Standard Errors

| Variable | Coefficient | Std. Error | P |
| --- | --- | --- | --- |
| (n-n') | −10.5049 | 2.9555 | 0.000379 |
| tg1_rapa | 0.3822 | 0.1416 | 0.006963 |
| Constant | −9.3555 | | |
| Variables not included in the model | | | |
| f_Div_R | | | |

Table 1.3—Odds Ratios and 95% Confidence Intervals

| Variable | Odds Ratio | 95% CI |
| --- | --- | --- |
| (n-n') | 0 | 0.0000 to 0.0090 |
| tg1_rapa | 1.4655 | 1.1103 to 1.9345 |

Table 1.4—Classification table (cut-off value p = 0.5)

| | Predicted group | | |
| --- | --- | --- | --- |
| Actual group | 0 | 1 | Percent correct |
| Y = 0 | 38 | 5 | 88.37% |
| Y = 1 | 10 | 16 | 61.54% |
| Percent of cases correctly classified | | | 78.26% |

Table 1.5—ROC curve analysis

| | |
| --- | --- |
| Area under the ROC curve (AUC) | 0.836 |
| Standard error | 0.0538 |
| 95% Confidence interval | 0.728 to 0.914 |
| ROC curve | |

| Variable | Odds |
| --- | --- |
| Classification variable | DG_ROC |
| Positive group | |
| DG_ROC = | 1 |
| Sample size | 26 |
| Negative group | |
| DG_ROC = | 0 |
| Sample size | 43 |
| Disease prevalence (%) | 15 |
| Area under the ROC curve (AUC) | 0.836 |
| Standard error | 0.0473 |
| 95% Confidence interval | 0.728 to 0.914 |
| z statistic | 7.106 |
| Significance level P (Area = 0.5) | 0.0001 |

Step ii—apoE Genotyping

ApoE genotyping was carried out by PCR amplification of genomic DNA with ApoE forward and reverse primers which flank the polymorphic loci, following by restriction enzyme digestion of the PCR products with the enzyme Cfo 1. Due to the nucleotide sequence variation, PCR products amplified from the different apoE alleles give rise to restriction fragments of different lengths when digested with Cfo 1. Hence, restriction fragments derived from each of the different alleles (and different combinations thereof) give characteristic banding patterns when resolved by agarose gel electrophoresis.

Genomic DNA for genotyping was extracted from a sample of whole blood (or PBLs) taken from the test subject.

If a blood sample is to be taken from the subject for the purposes of assessing the cell cycle defect at G1/S, then conveniently a small volume of this sample can be removed for DNA extraction. The extracted blood was diluted 1:5 with PBS and the tubes immersed in boiling water for 10 minutes. The samples were then spun at 15,000 g for 10 minutes. The supernatant was used directly for genotyping by PCR.

PCR reactions were assembled in 96-well plates, to give the following reaction composition, per well:

| | |
|---|---|
| APOE (Forward Primer) | 0.1 µl (100 µM) |
| APOE' (Reverse Primer) | 0.1 µl (100 µM) |
| Molecular Biology Grade Water | 5.8 µl |
| Dimethyl Sulfoxide | 2 µl |
| ABGene Reddy Mix (AB-0575/DC/LD/B) | 10 µl |
| Test DNA | 2 µl |
| TOTAL | 20 µl |

2× Reddymix PCR master mix (Thermo scientific, AB-0575/DC/LD/B)

Final Composition:

| | | |
|---|---|---|
| 0.625 | units | ThermoPrime Taq DNA polymerase |
| 75 | mM | Tris-HCl (pH 8.8 at 25° C.) |
| 20 | mM | (NH4) 2SO4 |
| 1.5 | Mm | MgCl2 |
| 0.01% | (v/v) | Tween 20 |
| 0.2 | mM | each of dATP, dCTP, dGTP and dTTP. |

Precipitant and red dye for electrophoresis.

ApoE forward primer (100 µM) (Sigma Genosys)
(SEQ ID NO: 1)
Sequence: 5'-TCCAAGGAGCTGCAGGCGGCGCA-3'

ApoE reverse primer (100 µM) (Sigma Genosys)
(SEQ ID NO: 2)
Sequence: 5'-ACAGAATTCGCCCCGGCCTGGTACACTGCCA-3'

Thermocycling was then carried out using the programme: 95° C. for 5 min, followed by 40 cycles of 95° C. for 1 min, 65° C. for 30 sec and 72° C. for 30 sec.

Following the PCR, plates were stored at +4° C.

Restriction enzyme reactions were assembled as follows (per individual PCR reaction):

| | |
|---|---|
| Enzyme Cfo 1(Hha I) | 1 µl |
| Buffer L (Roche) | 2 µl |
| PCR reaction | 17 µl |
| TOTAL | 20 µl |

Reactions were incubated at 37° C. overnight, then stored at 4° C. overnight

The digestion products were analysed by gel electrophoresis on a mixture of Metaphor® and multipurpose agarose (12.48 g Metaphor and 2.52 g multipurpose agarose in 300 ml 1×TBE with SYBR Safe DNA staining).

The banding patterns were used to determine the ApoE genotype of the individual. FIG. 1 is a representative agarose gel which shows the characteristic banding patterns for each apoE genotype.

The reagents used for restriction enzyme digestion and agarose gel electrophoresis were as follows:
Nuclease free water (Qiagen, 129114)
Dimethyl Sulfoxide (Sigma, D8418)
Restriction endonuclease Cfol (Hha I), 10 U/µl (Roche, 10688 541 001)
Buffer L, provided with Cfo I kit (Roche, 10688 541 001)
10×TBE (Tris Boric acid EDTA) buffer (Invitrogen, 15581-028) (Composition: 1.0M Tris, 0.9M boric acid, 0.01 M EDTA).
Multipurpose agarose (Roche, 11388991001)
Metaphor agarose (Lonza, cat. no: 50184)
SYBR safe DNA gel stain (Invitrogen, s33102) (10,000× conc in DMSO)
6× type II gel loading buffer (Thermo scientific, AB-0594)
Molecular weight marker V (Roche, 10821705001), (8-587 base pairs)

For any individual test subject, the result or "outcome measure" of the apoE genotyping assay is simply expressed as a confirmed apoE genotype for the test subject, which will be one of the following: apoE 2/2, apoE 2/3, apoE 2/4, apoE 3/3, apoE 3/4, or apoE 4/4. However, when viewed across a screening population, the number of apoE4 alleles present in a test subject may be treated as a "variable" for the purposes of statistical analysis.

TABLE 2

Figure 2A:
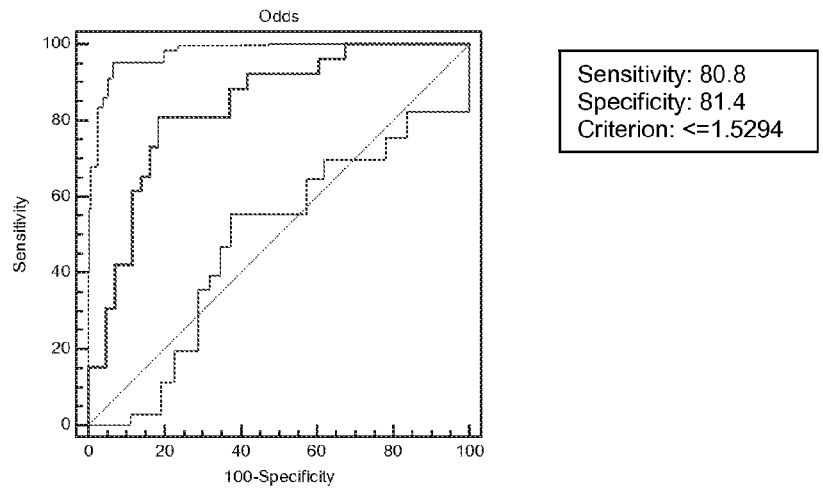
FIG. 2 illustrates the sensitivity and specificity of a diagnostic prediction for risk of developing Alzheimer's disease, wherein the diagnostic prediction is based on A) Lymphocyte test alone; B) presence and number of ApoE4 alleles alone (Table 2); C). combining the results of a lymphocyte culture assay (to assess the cell cycle regulatory defect at G1/S) and apoE4 genotyping.
Figure 2B:
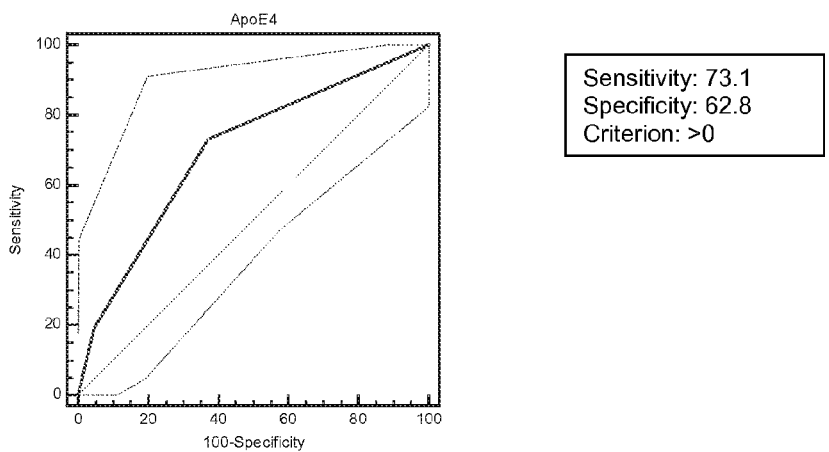

ROC curve to determine the sensitivity and specificity of the ApoE genotyping alone in the present cohort (FIG. 2B).

| | | |
|---|---|---|
| Sample size | | 69 |
| Positive group: | DG_ROC = 1 | 26 |
| Negative group: | DG_ROC = 0 | 43 |
| Area under the ROC curve (AUC) | | 0.698 |
| Standard Error a | | 0.0602 |
| 95% Confidence Interval b | | 0.576 to 0.803 |
| z statistic | | 3.291 |
| Significance level P (Area = 0.5) | | 0.0010 |

| Criterion | Sensitivity | 95% CI | Specificity | 95% CI | +LR | −LR |
|---|---|---|---|---|---|---|
| >=0 | 100.00 | 86.8-100.0 | 0.00 | 0.0-8.2 | 1.00 | |
| >0 * | 73.08 | 52.2-88.4 | 62.79 | 46.7-77.0 | 1.96 | 0.43 |
| >1 | 19.23 | 6.6-39.4 | 95.35 | 84.2-99.4 | 4.13 | 0.85 |
| >2 | 0.00 | 0.0-13.2 | 100.00 | 91.8-100.0 | | 1.00 | a DeLong et al., 1988
b Binomial exact

The Effect of the ApoE4 Status on the Outcome of the Lymphocyte Test.

Figure 3A:
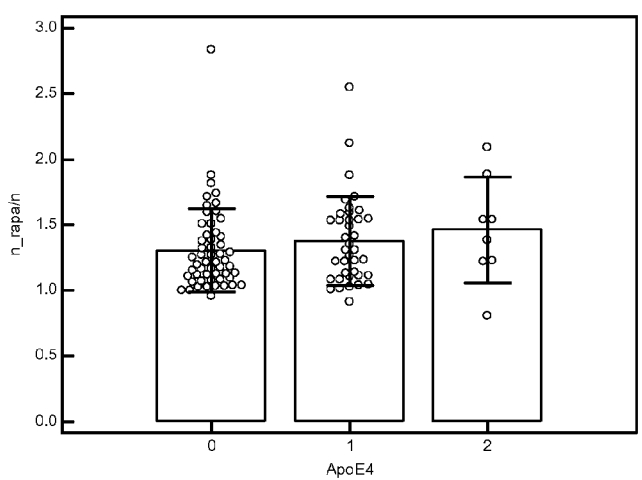
FIG. 3 shows that the number of apoE4 alleles possessed by an individual does not affect the results of the lymphocyte test when measuring: A) the number of cell divisions under the effect of Rapamycin relative to control cultures from the same individual ("n_rapa/n")(Table 3); B) the length of the G1 time under the effect of Rapamycin ("TG1_Rapa")(Table 4); C) the odds of a person being AD or not based on the rapamycin test alone ("Odds")(Table 5)
Figure 3B:
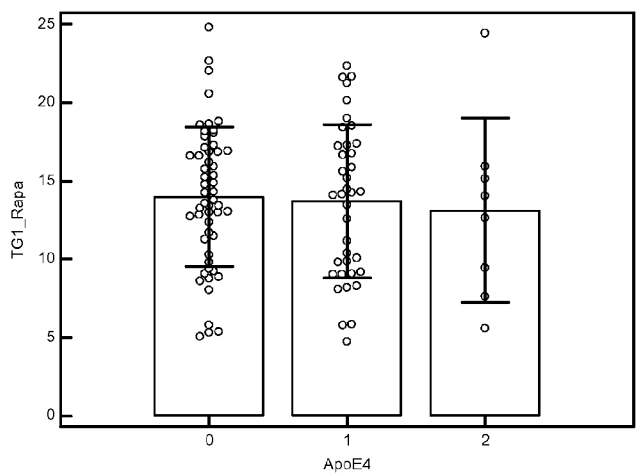
Figure 3C:
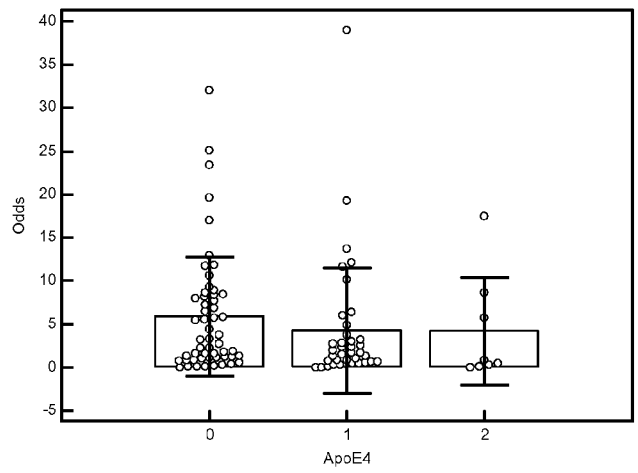

As mentioned above, the results of step (i) are not dependent upon the underlying apoE4 genotype. Tables 3, 4 and 5 and FIGS. 3A, 3B and 3C confirm that this is the case.

TABLE 3

One-way analysis of variance (variable: "n rapa/n" = change in the number of cell divisions under the effect of Rapamycin relative to control cultures from the same individual; Factor: number of ApoE4 alleles) (Sample size = 100)

Table 3.1—Levene's Test for Equality of Variances

| | |
|---|---|
| Levene statistic | 0.682 |
| DF 1 | 2 |
| DF 2 | 97 |
| Significance level | P = 0.508 |

Table 3.2—ANOVA

| Source of variation | Sum of squares | DF | Mean square |
|---|---|---|---|
| Between groups (influence factor) | 0.2395 | 2 | 0.1198 |

TABLE 3-continued

One-way analysis of variance (variable: "n rapa/n" = change in the number of cell divisions under the effect of Rapamycin relative to control cultures from the same individual; Factor: number of ApoE4 alleles) (Sample size = 100)

| | | | |
|---|---|---|---|
| Within groups (other fluctuations) | 10.584 | 97 | 0.1091 |
| Total | 10.8236 | 99 | |
| F-ratio | 1.098 | | |
| Significance level | P = 0.338 | | |

| Factor | n | Mean |
|---|---|---|
| (1) 0 | 54 | 1.3044 |
| (2) 1 | 38 | 1.3775 |
| (3) 2 | 8 | 1.4624 |

TABLE 4

One-way analysis of variance (variable: "TG1 Rapa" = length of the G1 time under the effect of Rapamycin; Factor: number of ApoE4 alleles)(Sample Size = 100)

Table 4.1—Levene's Test for Equality of Variances

| | |
|---|---|
| Levene statistic | 0.67 |
| DF 1 | 2 |
| DF 2 | 97 |
| Significance level | P = 0.514 |

Table 4.2—ANOVA

| Source of variation | Sum of squares | DF | Mean square |
|---|---|---|---|
| Between groups (influence factor) | 6.2291 | 2 | 3.1145 |
| Within groups (other fluctuations) | 2174.3258 | 97 | 22.4157 |
| Total | 2180.5548 | 99 | |
| F-ratio | 0.139 | | |
| Significance level | P = 0.870 | | |

| Factor | n | Mean |
|---|---|---|
| (1) 0 | 54 | 13.9944 |
| (2) 1 | 38 | 13.7038 |
| (3) 2 | 8 | 13.1059 |

TABLE 5

One-way analysis of variance (variable: "Odds" = The odds of a person being AD or not based on the rapamycin test alone; Factor: number of ApoE4 alleles)(Sample Size = 100)

Table 5.1—Levene's Test for Equality of Variances

| | |
|---|---|
| Levene statistic | 0.131 |
| DF 1 | 2 |
| DF 2 | 97 |
| Significance level | P = 0.877 |

Table 5.2—ANOVA

| Source of variation | Sum of squares | DF | Mean square |
|---|---|---|---|
| Between groups (influence factor) | 64.999 | 2 | 32.4995 |
| Within groups (other fluctuations) | 4736.2797 | 97 | 48.8276 |
| Total | 4801.2787 | 99 | |
| F-ratio | 0.666 | | |
| Significance level | P = 0.516 | | |

TABLE 5-continued

One-way analysis of variance (variable: "Odds" = The odds of a person being AD or not based on the rapamycin test alone; Factor: number of ApoE4 alleles)(Sample Size = 100)

| Factor | n | Mean |
|---|---|---|
| (1) 0 | 54 | 5.8613 |
| (2) 1 | 38 | 4.2587 |
| (3) 2 | 8 | 4.1755 |

Statistical Analysis of Results for Single and Combined Assays, and Derivation of Diagnostic Predictor Considering first the results of the lymphocyte culture assay (step i) alone:

Based on the combination of the difference between the number of cell divisions in the rapamycin vs. control cultures (n—from LDH assay) and the effect of relative lengthening of the G1 time after treatment with rapamycin (TG1_Rapa), 78.26% of AD patients were identified correctly.

Based on the relationship between the variables the logitp=0.3822(TG1_Rapa)−10.5049*(n-n')−9.3555, we calculate $p=1/(1+e^{-logitp})$. Based on this relation, the odds of a person being a control with this particular set of results is: $p/(1-p)$.

ROC curve analysis was carried out to establish the cut-off point at which patients would be classified as AD versus Control. The value for the area under the ROC curve indicates that a randomly selected individual from the positive group has a test value different than that for a randomly chosen individual from the negative group 83.6% of the time (Zweig & Campbell, 1993).

The lymphocyte culture test on its own allows the calculation of the risk for developing AD. This is represented by the "odds" of staying healthy with a particular test result.

Logistic regression was then used to statistically combine the results of the lymphocyte culture test, i.e. the calculated "odds" value, with apoE4 genotype, by treating apoE4 genotype (in particular the number of Apo E4 alleles) as a co-variable, as shown in Table 6. In simple terms, the logistic regression analysis indicated that both variables contribute significantly to predicting the correct diagnosis (DG-ROC). The logistic regression allows one to calculate the contribution of each variable, and based on those values one can calculate a new algorithm (diagnostic predictor) for the diagnostic prediction which includes both the "odds" predicted by the lymphocyte culture test and the ApoE4 genotype (i.e. the number of apoE4 alleles). This new predictor is then subject to ROC analysis to confirm the accuracy and significance of the prediction.

TABLE 6 logistic regression of independent cell culture and genotyping assay results

| Logistic regression | |
|---|---|
| Dependent Y | Dg_roc |
| Method | Forward |
| Enter variable if P< | 0.05 |
| Remove variable if P> | 0.1 |
| Sample size | 67 |
| Cases with Y = 0 | 42 (62.69%) |
| Cases with Y = 1 | 25 (37.31%) |

TABLE 6-continued logistic regression of independent cell culture and genotyping assay results

Table 6.1—Overall Model Fit

| | |
|---|---|
| Null model −2 Log Likelihood | 88.52077 |
| Full model −2 Log Likelihood | 61.1708 |
| Chi-square | 27.35 |
| DF | 2 |
| Significance level | P < 0.0001 |

Table 6.2—Coefficients and Standard Errors

| Variable | Coefficient | Std. Error | P |
|---|---|---|---|
| ApoE4 | 1.2539 | 0.5239 | 0.0167 |
| Odds | −0.3547 | 0.1302 | 0.006436 |
| Constant | −0.2715 | | |
| Variables not included in the model | | | |
| P21 | | | |
| P27 | | | |
| Cdki | | | |

Table 6.3—Odds Ratios and 95% Confidence Intervals

| Variable | Odds Ratio | 95% CI |
|---|---|---|
| ApoE4 | 3.5039 | 1.2548 to 9.7843 |
| Odds | 0.7014 | 0.5435 to 0.9053 |

Table 6.4—Classification table (cut-off value p = 0.5)

| | Predicted group | | |
|---|---|---|---|
| Actual group | 0 | 1 | Percent correct |
| Y = 0 | 35 | 7 | 83.33% |
| Y = 1 | 7 | 18 | 72.00% |
| Percent of cases correctly classified | | | 79.10% |

Table 6.5—ROC curve analysis

| | |
|---|---|
| Area under the ROC curve (AUC) | 0.864 |
| Standard error | 0.0506 |
| 95% Confidence interval | 0.758 to 0.935 |

Based on the coefficients given by the logistic regression (in bold above) the new predictor can be calculated as:

$$\text{Predictor} = 1.2539 * \text{ApoE4} - 0.3547 * \text{Odds} - 0.2715$$

Where "ApoE4" is the number of ApoE4 alleles present, and the "Odds" is the odds of a person remaining control with a particular test result based on the original lymphocyte culture assay.

This new 'predictor' is used for the ROC curve, shown in Table 7. Bold numbers below indicate the characteristics of the new predictor.

TABLE 7 derivation of area under the ROC curve (AUC) using new (combined) predictor ROC curve

| | |
|---|---|
| Variable | 1.2539*ApoE4 − 0.3547*Odds − 0.2715 |
| Classification variable | DG_ROC |
| Positive group | |
| DG_ROC = | 1 |
| Sample size | 26 |
| Negative group | |
| DG_ROC = | 0 |
| Sample size | 43 |
| Disease prevalence (%) | 15 |
| Area under the ROC curve (AUC) | 0.858 |
| Standard error | 0.0506 |
| 95% Confidence interval | 0.753 to 0.930 |
| z statistic | 7.065 |
| Significance level P (Area = 0.5) | 0.0001 |

Criterion values and coordinates of the ROC curve

| Criterion | Sensitivity | 95% CI | Specificity | 95% CI | +LR | −LR | +PV | 95% CI | −PV | 95% CI |
|---|---|---|---|---|---|---|---|---|---|---|
| >=−11.6319 | 100.00 | 86.7-100.0 | 0.00 | 0.0-8.3 | 1.00 | | 15.0 | 7.6-25.6 | | |
| >−3.1125 | 100.00 | 86.7-100.0 | 37.21 | 23.0-53.3 | 1.59 | 0.00 | 21.9 | 11.2-36.4 | 100.0 | 83.7-100.0 |
| >−2.8291 | 96.15 | 80.3-99.4 | 37.21 | 23.0-53.3 | 1.53 | 0.10 | 21.3 | 10.6-35.8 | 98.2 | 81.3-98.1 |
| >−1.2448 | 96.15 | 80.3-99.4 | 53.49 | 37.7-68.8 | 2.07 | 0.072 | 26.7 | 13.6-43.8 | 98.7 | 86.4-98.6 |
| >−1.0643 | 92.31 | 74.8-98.8 | 53.49 | 37.7-68.8 | 1.98 | 0.14 | 25.9 | 12.8-43.2 | 97.5 | 84.7-99.4 |
| >−0.8408* | 92.31 | 74.8-98.8 | 65.12 | 49.1-79.0 | 2.65 | 0.12 | 31.8 | 16.2-51.3 | 98.0 | 87.1-99.5 |
| >−0.814 | 84.62 | 65.1-95.5 | 65.12 | 49.1-79.0 | 2.43 | 0.24 | 30.0 | 14.5-49.7 | 96.0 | 84.3-99.5 |
| >−0.7399 | 84.62 | 65.1-95.5 | 67.44 | 51.5-80.9 | 2.60 | 0.23 | 31.4 | 15.1-52.0 | 96.1 | 84.9-99.5 |
| >−0.7088 | 80.77 | 60.6-93.4 | 67.44 | 51.5-80.9 | 2.48 | 0.29 | 30.4 | 14.4-51.0 | 95.2 | 83.6-99.3 |
| >−0.6899 | 80.77 | 60.6-93.4 | 69.77 | 53.9-82.8 | 2.67 | 0.28 | 32.0 | 15.3-53.1 | 95.4 | 84.0-99.3 |
| >−0.662 | 76.92 | 56.3-91.0 | 69.77 | 53.9-82.8 | 2.54 | 0.33 | 31.0 | 14.2-52.5 | 94.5 | 82.9-99.0 |
| >−0.6383 | 76.92 | 56.3-91.0 | 72.09 | 56.3-84.7 | 2.76 | 0.32 | 32.7 | 15.2-54.7 | 94.7 | 83.4-99.1 |
| >−0.5751 | 73.08 | 52.2-88.4 | 72.09 | 56.3-84.7 | 2.62 | 0.37 | 31.6 | 14.1-54.1 | 93.8 | 82.4-98.7 |
| >−0.5163 | 73.08 | 52.2-88.4 | 74.42 | 58.8-86.5 | 2.86 | 0.36 | 33.5 | 15.1-56.6 | 94.0 | 82.8-98.8 |
| >−0.4531 | 69.23 | 48.2-85.6 | 74.42 | 58.8-86.5 | 2.71 | 0.41 | 32.3 | 14.3-55.4 | 93.2 | 81.7-98.4 |
| >−0.0644 | 69.23 | 48.2-85.6 | 83.72 | 69.3-93.2 | 4.25 | 0.37 | 42.9 | 19.2-69.3 | 93.9 | 83.6-98.6 |
| >0.0026 | 65.38 | 44.3-82.8 | 83.72 | 69.3-93.2 | 4.02 | 0.41 | 41.5 | 18.1-68.1 | 93.2 | 82.6-98.3 |
| >0.0911 | 65.38 | 44.3-82.8 | 86.05 | 72.1-94.7 | 4.69 | 0.40 | 45.3 | 19.5-73.1 | 93.4 | 83.1-98.3 |

TABLE 7-continued derivation of area under the ROC curve (AUC) using new (combined) predictor

| >0.1468 | 61.54 | 40.6-79.7 | 86.05 | 72.1-94.7 | 4.41 | 0.45 | 43.8 | 18.4-71.8 | 92.7 | 82.2-97.9 |
| >0.391 | 61.54 | 40.6-79.7 | 93.02 | 80.9-98.5 | 8.82 | 0.41 | 60.9 | 27.1-88.1 | 93.2 | 83.4-98.1 |
| >0.4552 | 57.69 | 36.9-76.6 | 93.02 | 80.9-98.5 | 8.27 | 0.45 | 59.3 | 25.8-87.2 | 92.6 | 82.6-97.8 |
| >0.5124 | 57.69 | 36.9-76.6 | 95.35 | 84.2-99.3 | 12.40 | 0.44 | 68.6 | 29.6-93.8 | 92.7 | 83.0-97.8 |
| >0.7048 | 42.31 | 23.4-63.1 | 95.35 | 84.2-99.3 | 9.10 | 0.61 | 61.6 | 21.8-91.7 | 90.4 | 80.0-96.4 |
| >0.7273 | 42.31 | 23.4-63.1 | 97.67 | 87.7-99.6 | 18.19 | 0.59 | 76.2 | 25.9-96.7 | 90.6 | 80.5-96.5 |
| >1.9511 | 11.54 | 2.6-30.2 | 97.67 | 87.7-99.6 | 4.96 | 0.91 | 46.7 | 8.4-91.9 | 86.2 | 75.5-93.5 |
| >2.073 | 11.54 | 2.6-30.2 | 100.00 | 91.7-100.0 |  | 0.88 | 100.0 | 16.5-100.0 | 86.5 | 75.9-93.6 |
| >2.2347 | 0.00 | 0.0-13.3 | 100.00 | 91.7-100.0 |  | 1.00 |  |  | 85.0 | 74.4-92.4 |

+LR Positive likelihood ratio
−LR Negative likelihood ratio
+PV Positive predictive value
−PV Negative predictive value It can be derived that the addition of the apoE4 genotype result to the odds calculated from the lymphocyte culture result leads to an increased accuracy of the diagnosis: 85.8% area under the curve in the ROC curve.

Figure 2C:
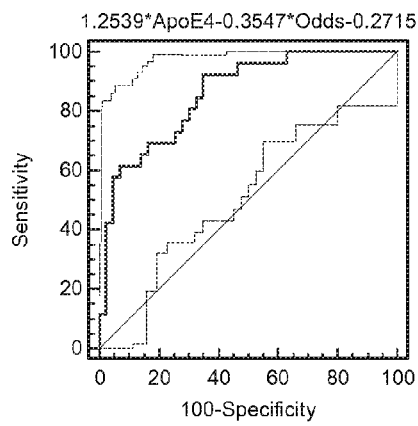

FIG. 2C illustrates sensitivity and specificity of an assay based on the new "combined" predictor derived above.

Example 2—Longitudinal Analysis

Retrospective longitudinal data (cognitive assessments and carer information) was obtained from OPTIMA regarding a subset of the patients included in the study described above. The data was obtained before the lymphocyte test of step (i) of the present method was carried out.

The cohort of patients with longitudinal follow up consists of probable AD and MCI (mild cognitive impairment patients).

Table 8 shows that probable AD patients have significantly earlier onset of memory problems than the MCI patients in this age-matched patient group. This data confirms that the cohort conforms to the expected pattern for probable AD and MCI patients.

TABLE 8

Age at disease onset (memory complaint)

Table 8.1

| | Factors | |
| --- | --- | --- |
| | MCI | Prob. AD |
| Sample size | 20 | 25 |
| Median survival | 80.08 | 70.2866 |

Table 8.2

| | Factors | | | |
| --- | --- | --- | --- | --- |
| | MCI | | Prob. AD | |
| Survival time | Survival Proportion | Standard Error | Survival Proportion | Standard Error |
| 51.74 | — | — | 0.96 | 0.0392 |
| 52.472 | — | — | 0.92 | 0.0543 |
| 53.6918 | — | — | 0.88 | 0.065 |
| 58.05 | — | — | 0.84 | 0.0733 |
| 59.89 | — | — | 0.8 | 0.08 |
| 61.4934 | — | — | 0.76 | 0.0854 |
| 61.64 | — | — | 0.72 | 0.0898 |
| 62.95 | 0.95 | 0.0487 | — | — |
| 63.31 | 0.9 | 0.0671 | — | — |
| 64.87 | — | — | 0.68 | 0.0933 |
| 68.126 | 0.85 | 0.0798 | — | — |

TABLE 8-continued

Age at disease onset (memory complaint)

| 68.2081 | — | — | 0.6 | 0.098 |
| 68.3178 | — | — | — | — |
| 68.51 | 0.797 | 0.0908 | — | — |
| 68.906 | — | — | 0.56 | 0.0993 |
| 69.63 | — | — | 0.52 | 0.0999 |
| 70.2866 | — | — | 0.48 | 0.0999 |
| 70.94 | — | — | 0.44 | 0.0993 |
| 72.05 | 0.744 | 0.0991 | — | — |
| 72.92 | 0.691 | 0.105 | — | — |
| 73 | — | — | 0.4 | 0.098 |
| 74.82 | — | — | 0.36 | 0.096 |
| 75.31 | 0.637 | 0.11 | — | — |
| 75.3706 | — | — | 0.32 | 0.0933 |
| 75.47 | — | — | 0.28 | 0.0898 |
| 75.58 | — | — | 0.24 | 0.0854 |
| 76.42 | — | — | 0.2 | 0.08 |
| 76.47 | — | — | 0.16 | 0.0733 |
| 77.3806 | — | — | 0.12 | 0.065 |
| 78.42 | 0.584 | 0.113 | — | — |
| 78.88 | — | — | 0.08 | 0.0543 |
| 79.02 | 0.531 | 0.114 | — | — |
| 80.08 | 0.478 | 0.115 | — | — |
| 80.1123 | 0.425 | 0.114 | — | — |
| 80.463 | 0.372 | 0.111 | — | — |
| 80.56 | 0.319 | 0.107 | — | — |
| 80.97 | 0.266 | 0.102 | — | — |
| 81.75 | — | — | 0.04 | 0.0392 |
| 82.74 | 0.213 | 0.0942 | — | — |
| 82.8959 | — | — | — | — |
| 83.663 | 0.142 | 0.0854 | — | — |
| 85.86 | — | — | 0 | 0 |
| 86.337 | 0.0708 | 0.0658 | — | — |
| 87.7123 | 0 | 0 | — | — |

Table 8.3—Comparison of survival curves (Logrank test)

| | Factors | |
| --- | --- | --- |
| | MCI | Prob. AD |
| Endpoint: Observed n | 18 | 25 |
| Expected n | 27.2 | 15.8 |
| Chi-square | 9.26 | |
| DF | 1 | |
| Significance | P = 0.0023 | |
| Hazard ratio | 2.3804 | |
| 95% CI | 1.2810 to 4.4232 | |

Figure 4:
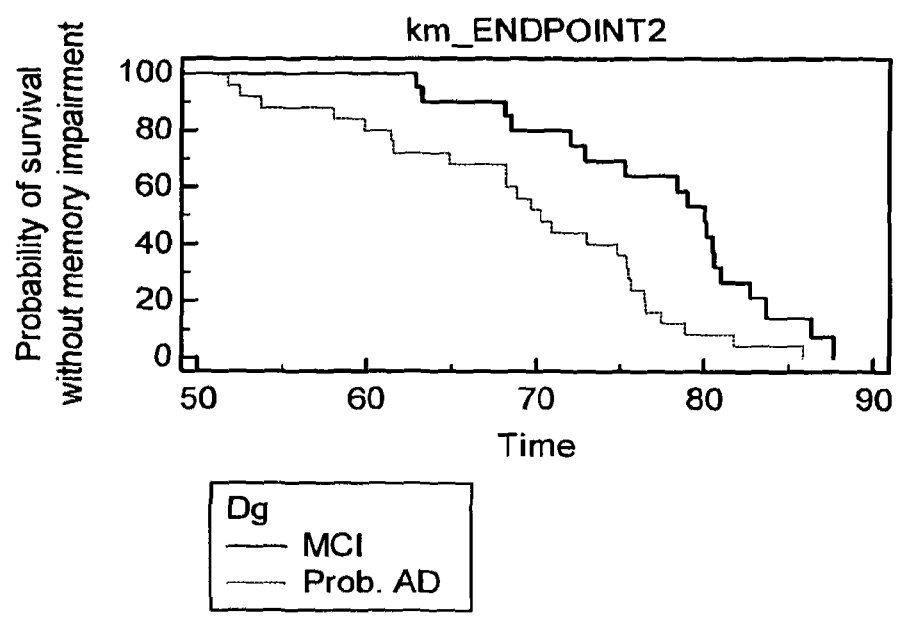
FIG. 4 shows a KM curve for the data in Table 8. This indicates that in this cohort the probability of being free of memory problems at any age is much lower if the diagnosis is probable AD than with a diagnosis of MCI.
Figure 5:
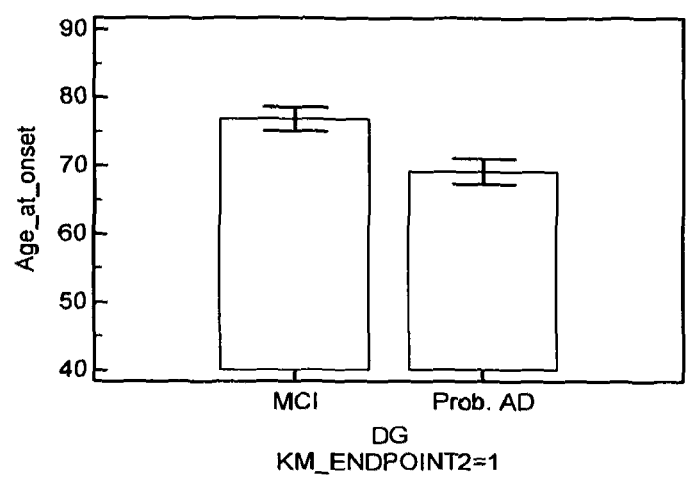
FIG. 5 illustrates the mean age at onset of memory impairment in MCI and probable AD (data given in Table 9.3).

The data in Table 8 is represented in a KM curve in FIG. 4. This indicates that in this cohort the probability of being free of memory problems at any age is much lower if the diagnosis is probable AD than with a diagnosis of MCI. Table 9 shows the same data using the ANOVA test (see also FIG. 5).

TABLE 9

Age at disease onset (memory complaint) - One-way analysis of variance (Sample size = 43).

Table 9.1—Levene's Test for Equality of Variances

| | |
|---|---|
| Levene statistic | 0.796 |
| DF 1 | 1 |
| DF 2 | 41 |
| Significance level | P = 0.378 |

Table 9.2—ANOVA

| Source of variation | Sum of squares | DF | Mean square |
|---|---|---|---|
| Between groups (influence factor) | 605.4736 | 1 | 605.4736 |
| Within groups (other fluctuations) | 2966.8656 | 41 | 72.3626 |
| Total | 3572.3392 | 42 | |
| F-ratio | 8.367 | | |
| Significance level | P = 0.006 | | |

Table 9.3—Student-Newman-Keuls test for all pairwise comparisons

| Factor | n | Mean | Different (P < 0.05) from factor nr |
|---|---|---|---|
| (1) MCI | 18 | 76.8474 | −2 |
| (2) PROB. AD | 25 | 69.2411 | −1 |

Figure 6:
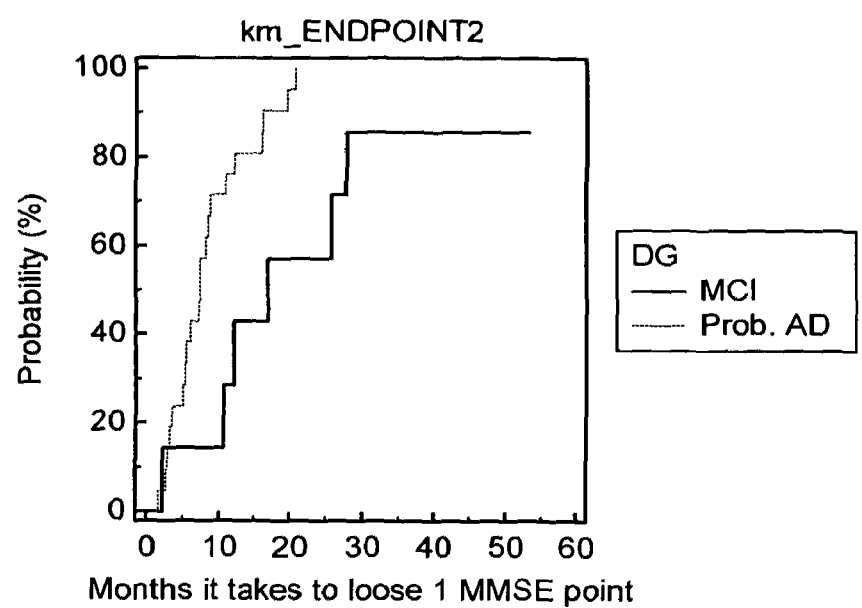
FIG. 6 illustrates the probability of losing 1 point on the MMSE scale within a certain period of time in AD and MCI patients (Table 10).

Table 10 shows an analysis of the time it takes (on average) to lose 1 point on the Mini-Mental State Examination (MMSE). In AD patients this period (Duration) lasts from the onset of memory problems to the point of entry into the study (when dementia was diagnosed). In MCI patients this period lasts from the onset of memory problems to point of first detectable cognitive deficit: MMSE=27 (during the follow up). Since AD accelerates as the disease gets more severe, and the AD patients are in more advanced stage of the disease, it is to be expected that time it takes to deteriorate 1 point on the MMSE scale takes significantly longer in the MCI patients. This is illustrated graphically in FIG. 6 (probability of losing 1 point on the MMSE scale within a certain period of time in AD and MCI patients).

Figure 7:
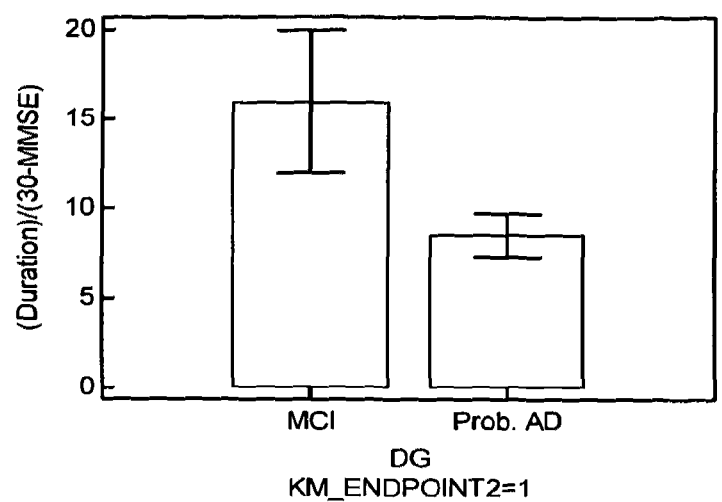
FIG. 7 shows the mean number of months taken to lose 1 point on the MMSE for MCI and probable AD (data given in Table 11.3).

Table 11 and FIG. 7 show the same data analysed using the ANOVA.

TABLE 10

Months to lose 1 MMSE point (AD patients from onset of memory problems to point of entry in study; MCI patients from onset of memory problems to point of first detectable cognitive deficit: MMSE = 27)

Table 10.1

| | Factors | |
|---|---|---|
| | MCI | Prob. AD |
| Sample size | 7 | 21 |
| Median Time required to lose 1 point on the MMSE scale | 16.9425 | 7.293 |

TABLE 10-continued

Months to lose 1 MMSE point (AD patients from onset of memory problems to point of entry in study; MCI patients from onset of memory problems to point of first detectable cognitive deficit: MMSE = 27)

Table 10.2

| | Factors | | | |
|---|---|---|---|---|
| | MCI | | Prob. AD | |
| Time required to lose 1 point on the MMSE scale | Proportion | Standard Error | Proportion | Standard Error |
| 1.5379 | — | — | 0.952 | 0.0465 |
| 2.1808 | 0.857 | 0.132 | — | — |
| 2.7462 | — | — | 0.905 | 0.0641 |
| 2.8855 | — | — | 0.857 | 0.0764 |
| 3.1377 | — | — | 0.81 | 0.0857 |
| 3.4976 | — | — | 0.762 | 0.0929 |
| 4.923 | — | — | 0.714 | 0.0986 |
| 5.2436 | — | — | 0.667 | 0.103 |
| 5.3782 | — | — | 0.619 | 0.106 |
| 6.1566 | — | — | 0.571 | 0.108 |
| 7.2745 | — | — | 0.524 | 0.109 |
| 7.293 | — | — | 0.476 | 0.109 |
| 7.3441 | — | — | 0.429 | 0.108 |
| 8.2022 | — | — | 0.381 | 0.106 |
| 8.4529 | — | — | 0.333 | 0.103 |
| 8.8726 | — | — | 0.286 | 0.0986 |
| 10.7266 | 0.714 | 0.171 | — | — |
| 11.029 | — | — | 0.238 | 0.0929 |
| 12.1233 | 0.571 | 0.187 | — | — |
| 12.1636 | — | — | 0.19 | 0.0857 |
| 15.9502 | — | — | 0.143 | 0.0764 |
| 16.1008 | — | — | 0.0952 | 0.0641 |
| 16.9425 | 0.429 | 0.187 | — | — |
| 19.5985 | — | — | 0.0476 | 0.0465 |
| 20.8169 | — | — | 0 | 0 |
| 25.9178 | 0.286 | 0.171 | — | — |
| 27.8466 | 0.143 | 0.132 | — | — |
| 53.2932 | — | — | — | — |

Table 10.3—Comparison of survival curves (Logrank test)

| | Factors | |
|---|---|---|
| | MCI | Prob. AD |
| Endpoint: Observed n | 6 | 21 |
| Expected n | 12 | 15 |
| Chi-square | 6.546 | |
| DF | 1 | |
| Significance | P = 0.0105 | |
| Hazard ratio | 2.8015 | |
| 95% CI | 1.3114 to 5.9849 | |

TABLE 11

One-way analysis of variance. Time required to lose 1 point on the MMSE scale (Sample size = 27)

Table 11.1—Levene's Test for Equality of Variances

| | |
|---|---|
| Levene statistic | 3.608 |
| DF 1 | 1 |
| DF 2 | 25 |
| Significance level | P = 0.069 |

Table 11.2—ANOVA

| Source of variation | Sum of squares | DF | Mean square |
|---|---|---|---|
| Between groups (influence factor) | 259.1003 | 1 | 259.1003 |

TABLE 11-continued

One-way analysis of variance. Time required to lose
1 point on the MMSE scale (Sample size = 27)

| | | | |
|---|---|---|---|
| Within groups (other fluctuations) | 1091.4025 | 25 | 43.6561 |
| Total | 1350.5028 | 26 | |
| F-ratio | 5.935 | | |
| Significance level | P = 0.022 | | |

Table 11.3—Student-Newman-Keuls test for all pairwise comparisons

| Factor | n | Mean | Different (P < 0.05) from factor nr |
|---|---|---|---|
| (1) MCI | 6 | 15.9563 | −2 |
| (2) PROB. AD | 21 | 8.505 | −1 |

Since only 7 MCI patients have reached the point of detectable cognitive deficit (MMSE=27), no further analysis was carried out for these patients.

Twenty-one (21) AD patients with full data sets were used for further analysis of the Lymphocyte test alone (DG_Odds), ApoE4 (ApoE4) status alone and the combination of the two (DG_Ly_ApoE).

Table 12 illustrates that the median time required to lose 1 point on the MMSE scale was significantly longer in patients who tested negative (0, n=4) on the lymphocyte test (lymphocyte test alone) than those who tested positive (1, n=17). The importance of this is that the lymphocyte test result is associated with significantly accelerated cognitive decline in AD patients. (The false negatives decline significantly slower).

Figure 8:
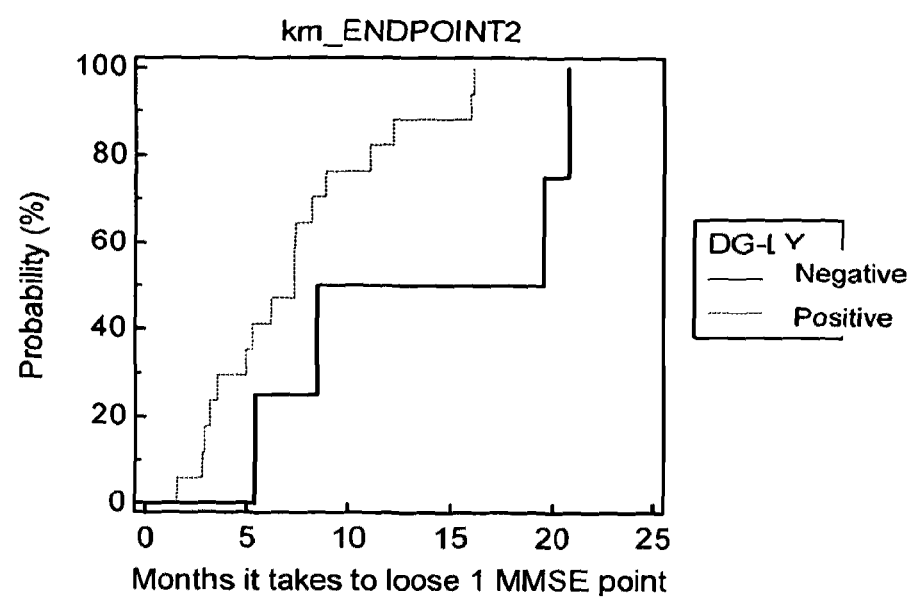
FIG. 8 illustrates the time required to lose 1 point on the MMSE scale for patients who tested negative (0, n=4) on the lymphocyte test (lymphocyte test alone) and those who tested positive (1, n=17) (Table 12).

FIG. 8 is the graphical representation of the data in Table 12. It shows that while 100% of AD patients who test positive lose the 1 point on the MMSE scale within ~17 months from onset, only ~50% of the patients who test negative lose the same 1 point on the MMSE scale during this time.

Figure 9:
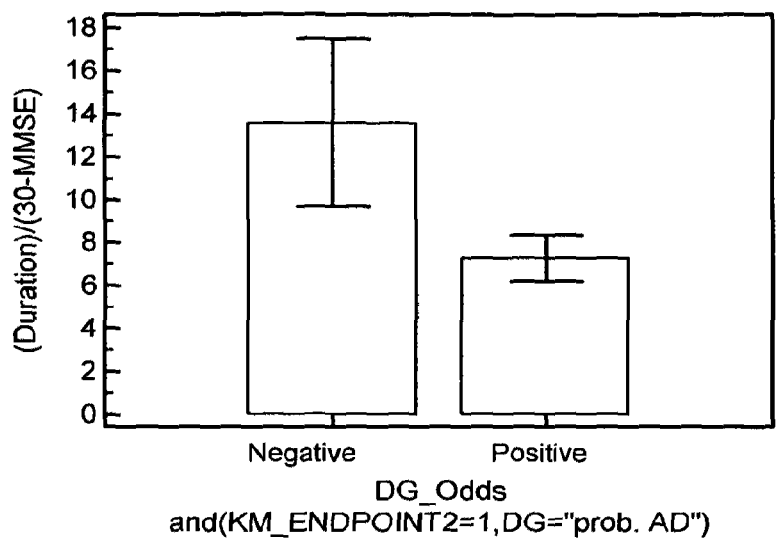
FIG. 9 shows the mean time required to lose 1 point on the MMSE scale for patients who tested negative (n=4) on the lymphocyte test (lymphocyte test alone) and those who tested positive (n=17) (Table 13.3).

Table 13 and FIG. 9 confirm this conclusion using an ANOVA test.

TABLE 12

Kaplan-Meier curve Time required
to lose 1 point on the MMSE scale

Table 12.1

| | Lymphocyte Test | |
|---|---|---|
| | Negative | Positive |
| Sample size | 4 | 17 |
| Median Time required to lose 1 point on the MMSE scale | 14.0257 | 7.2745 |

Table 12.2

| | Lymphocyte Test | | | |
|---|---|---|---|---|
| | Negative | | Positive | |
| Time required to lose 1 point on the MMSE scale | Proportion | Standard Error | Proportion | Standard Error |
| 1.5379 | — | — | 0.941 | 0.0571 |
| 2.7462 | — | — | 0.882 | 0.0781 |
| 2.8855 | — | — | 0.824 | 0.0925 |
| 3.1377 | — | — | 0.765 | 0.103 |
| 3.4976 | — | — | 0.706 | 0.111 |
| 4.923 | — | — | 0.647 | 0.116 |
| 5.2436 | — | — | 0.588 | 0.119 |
| 5.3782 | 0.75 | 0.217 | — | — |
| 6.1566 | — | — | 0.529 | 0.121 |
| 7.2745 | — | — | 0.471 | 0.121 |
| 7.293 | — | — | 0.412 | 0.119 |
| 7.3441 | — | — | 0.353 | 0.116 |
| 8.2022 | — | — | 0.294 | 0.111 |
| 8.4529 | 0.5 | 0.25 | — | — |
| 8.8726 | — | — | 0.235 | 0.103 |
| 11.029 | — | — | 0.176 | 0.0925 |
| 12.1636 | — | — | 0.118 | 0.0781 |
| 15.9502 | — | — | 0.0588 | 0.0571 |
| 16.1008 | — | — | 0 | 0 |
| 19.5985 | 0.25 | 0.217 | — | — |
| 20.8169 | 0 | 0 | — | — |

Table 12.3—Comparison of survival curves (Logrank test)

| | Lymphocyte Test | |
|---|---|---|
| | Negative | Positive |
| Endpoint: Observed n | 4 | 17 |
| Expected n | 7.8 | 13.2 |
| Chi-square | 3.8282 | |
| DF | 1 | |
| Significance | P = 0.0504 | |
| Hazard ratio | 2.5157 | |
| 95% CI | 1.0383 to 6.0954 | |

TABLE 13

One-way analysis of variance Time required to lose
1 point on the MMSE scale (Sample size = 21)

Table 13.1—Levene's Test for Equality of Variances

| | |
|---|---|
| Levene statistic | 5.377 |
| DF 1 | 1 |
| DF 2 | 19 |
| Significance level | P = 0.032 |

Table 13.2—ANOVA

| Source of variation | Sum of squares | DF | Mean square |
|---|---|---|---|
| Between groups (influence factor) | 126.3438 | 1 | 126.3438 |
| Within groups (other fluctuations) | 491.6702 | 19 | 25.8774 |
| Total | 618.0139 | 20 | |
| F-ratio | 4.882 | | |
| Significance level | P = 0.040 | | |

Table 13.3—Student-Newman-Keuls test for all pairwise comparisons

| Factor | n | Mean | Different (P < 0.05) from factor nr |
|---|---|---|---|
| (1) Negative | 4 | 13.5616 | −2 |
| (2) Positive | 17 | 7.3152 | −1 |

Table 14 shows that the median time required to lose 1 point on the MMSE scale was significantly shorter in patients who carry 1 or 2 ApoE4 alleles than those who do not have the ApoE4 allele.

Figure 10:
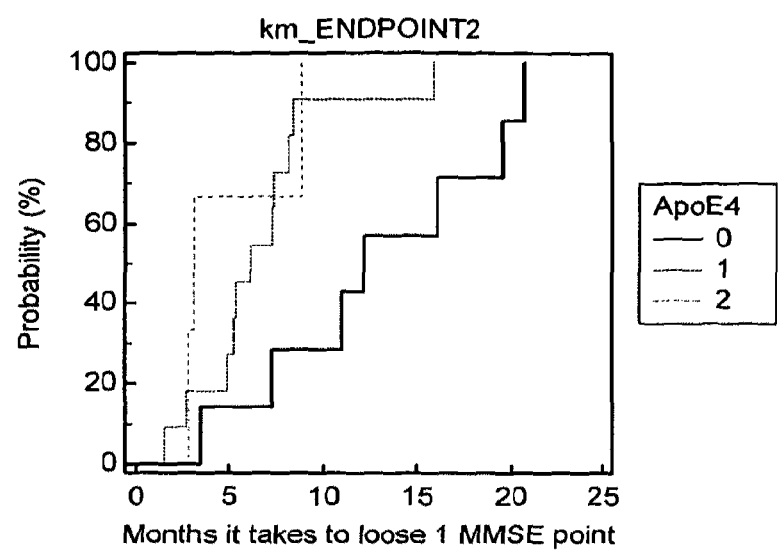
FIG. 10 illustrates the time required to lose 1 point on the MMSE scale for patients who carry 0, 1 or 2 ApoE4 alleles (Table 14).
Figure 11:
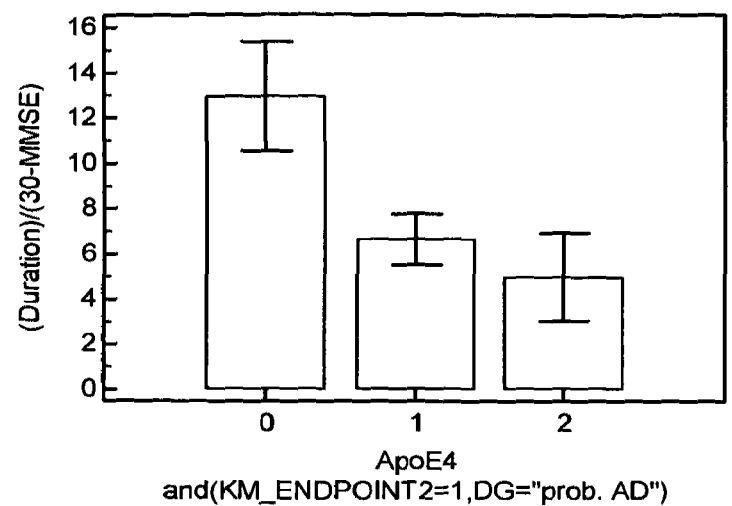
FIG. 11 shows the mean time required to lose 1 point on the MMSE scale for patients who carry 0, 1 or 2 ApoE4 alleles (Table 15.3).

FIG. 10 is the graphical representation of the data in Table 14. Table 15 and FIG. 11 confirm this conclusion using an ANOVA test.

TABLE 14

Kaplan-Meier curve Time required to lose 1 point on the MMSE scale

| | Number of ApoE4 Alleles | | |
|---|---|---|---|
| | 0 | 1 | 2 |
| Sample size | 7 | 11 | 3 |
| Median Time required to lose 1 point on the MMSE scale | 12.1636 | 6.1566 | 3.1377 |

| | Number of ApoE4 Alleles | | | | | |
|---|---|---|---|---|---|---|
| Time required to | 0 | | 1 | | 2 | |
| lose 1 point on the MMSE scale | Proportion | Standard Error | Proportion | Standard Error | Proportion | Standard Error |
| 1.5379 | — | — | 0.909 | 0.0867 | — | — |
| 2.7462 | — | — | 0.818 | 0.116 | — | — |
| 2.8855 | — | — | — | — | 0.667 | 0.272 |
| 3.1377 | — | — | — | — | 0.333 | 0.272 |
| 3.4976 | 0.857 | 0.132 | — | — | — | — |
| 4.923 | — | — | 0.727 | 0.134 | — | — |
| 5.2436 | — | — | 0.636 | 0.145 | — | — |
| 5.3782 | — | — | 0.545 | 0.15 | — | — |
| 6.1566 | — | — | 0.455 | 0.15 | — | — |
| 7.2745 | — | — | 0.364 | 0.145 | — | — |
| 7.293 | 0.714 | 0.171 | — | — | — | — |
| 7.3441 | — | — | 0.273 | 0.134 | — | — |
| 8.2022 | — | — | 0.182 | 0.116 | — | — |
| 8.4529 | — | — | 0.0909 | 0.0867 | — | — |
| 8.8726 | — | — | — | — | 0 | 0 |
| 11.029 | 0.571 | 0.187 | — | — | — | — |
| 12.1636 | 0.429 | 0.187 | — | — | — | — |
| 15.9502 | — | — | 0 | 0 | — | — |
| 16.1008 | 0.286 | 0.171 | — | — | — | — |
| 19.5985 | 0.143 | 0.132 | — | — | — | — |
| 20.8169 | 0 | 0 | — | — | — | — |

Comparison of survival curves (Logrank test)

| | Number of ApoE4 Alleles | | |
|---|---|---|---|
| | 0 | 1 | 2 |
| Endpoint: Observed n | 7 | 11 | 3 |
| Expected n | 12.3 | 7.1 | 1.6 |
| Chi-square | 5.796 | | |
| DF | 2 | | |
| Significance | $P = 0.0551$ | | |

Logrank test for trend

| | |
|---|---|
| Chi-square (trend) | 5.5218 |
| DF | 1 |
| Significance | $P = 0.0188$ |

TABLE 15

One-way analysis of variance Time required to lose 1 point on the MMSE scale (Sample Size = 21)

Table 15.1—Levene's Test for Equality of Variances

| | |
|---|---|
| Levene statistic | 1.968 |
| DF 1 | 2 |
| DF 2 | 18 |
| Significance level | $P = 0.169$ |

Table 15.2—ANOVA

| Source of variation | Sum of squares | DF | Mean square |
|---|---|---|---|
| Between groups (influence factor) | 212.19 | 2 | 106.095 |
| Within groups (other fluctuations) | 405.8239 | 18 | 22.5458 |
| Total | 618.0139 | 20 | |
| F-ratio | 4.706 | | |
| Significance level | $P = 0.023$ | | |

Table 15.3—Student-Newman-Keuls test for all pairwise comparisons

| Number of ApoE4 Alleles | n | Mean | Different ($P < 0.05$) from factor nr |
|---|---|---|---|
| (1) 0 | 7 | 12.9285 | −2 |
| (2) 1 | 11 | 6.6554 | −1 |
| (3) 2 | 3 | 4.9653 | |

Table 16 shows that the median time required to lose 1 point on the MMSE scale was significantly longer in patients who tested negative (0, n=2) on the lymphocyte+ApoE test (combined assay) than those who tested positive (1, n=19). The importance of this is that a positive test results with the combination assay (i.e. results above the cut-off established with reference to the ROC) is associated with significantly accelerated cognitive decline in AD patients. (The false negative decline significantly slower).

This analysis also shows that this relationship is stronger (p value is less than the same value for the 'lymphocyte test alone' or the ApoE genotype alone) when the combination assay is used rather than either assay (lymphocyte assay or ApoE genotyping) alone.

Figure 12:
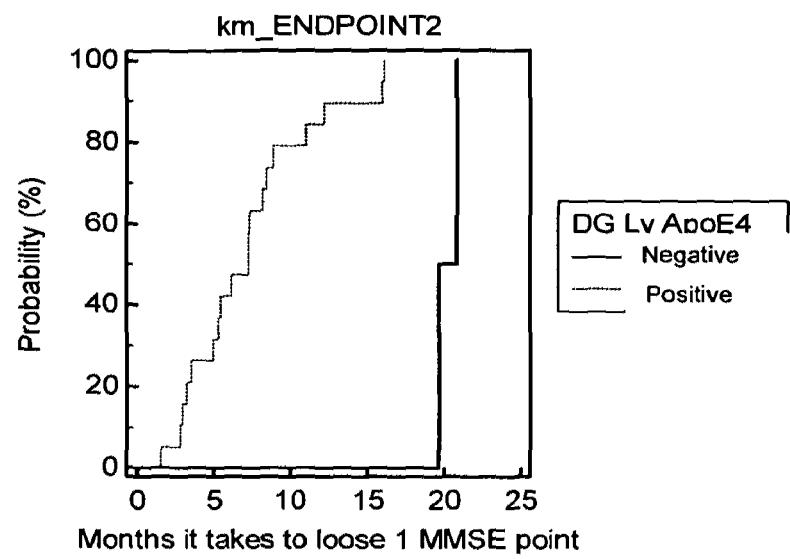
FIG. 12 illustrates time required to lose 1 point on the MMSE scale in patients who tested negative (0, n=2) on the lymphocyte+ApoE test (combined assay) and those who tested positive (1, n=19)(Table 16).
Figure 13:
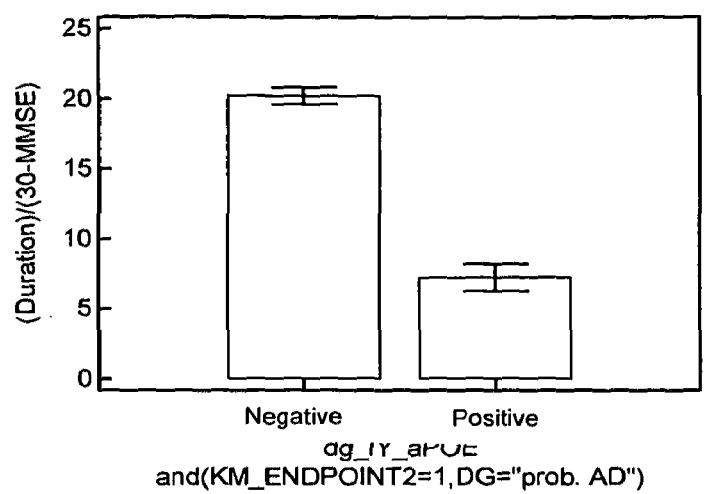
FIG. 13 shows the mean time required to lose 1 point on the MMSE scale in patients who tested negative (0, n=2) on the lymphocyte+ApoE test (combined assay) and those who tested positive (1, n=19) (Table 17.3).

FIG. 12 is the graphical representation of the data in Table 16. Table 17 and FIG. 13 show the same analysis using the ANOVA test.

TABLE 16

Kaplan-Meier curve Time required to lose 1 point on the MMSE scale

Table 16.1

| | Combined Test | |
| --- | --- | --- |
| | Negative | Positive |
| Sample size | 2 | 19 |
| Median Time required to lose 1 point on the MMSE scale | 20.2077 | 7.2745 |

Table 16.2

| | Combined Test | | | |
| --- | --- | --- | --- | --- |
| | Negative | | Positive | |
| Time required to lose 1 point on the MMSE scale | Proportion | Standard Error | Proportion | Standard Error |
| 1.5379 | — | — | 0.947 | 0.0512 |
| 2.7462 | — | — | 0.895 | 0.0704 |
| 2.8855 | — | — | 0.842 | 0.0837 |
| 3.1377 | — | — | 0.789 | 0.0935 |
| 3.4976 | — | — | 0.737 | 0.101 |
| 4.923 | — | — | 0.684 | 0.107 |
| 5.2436 | — | — | 0.632 | 0.111 |
| 5.3782 | — | — | 0.579 | 0.113 |
| 6.1566 | — | — | 0.526 | 0.115 |
| 7.2745 | — | — | 0.474 | 0.115 |
| 7.293 | — | — | 0.421 | 0.113 |
| 7.3441 | — | — | 0.368 | 0.111 |
| 8.2022 | — | — | 0.316 | 0.107 |
| 8.4529 | — | — | 0.263 | 0.101 |
| 8.8726 | — | — | 0.211 | 0.0935 |
| 11.029 | — | — | 0.158 | 0.0837 |
| 12.1636 | — | — | 0.105 | 0.0704 |
| 15.9502 | — | — | 0.0526 | 0.0512 |
| 16.1008 | — | — | 0 | 0 |
| 19.5985 | 0.5 | 0.354 | — | — |
| 20.8169 | 0 | 0 | — | — |

Table 16.3—Comparison of survival curves (Logrank test)

| | Combined Test | |
| --- | --- | --- |
| | Negative | Positive |
| Endpoint: Observed n | 2 | 19 |
| Expected n | 6.3 | 14.7 |
| Chi-square | 6.355 | |
| DF | 1 | |
| Significance | P = 0.0117 | |
| Hazard ratio | 4.0629 | |
| 95% CI | 1.5971 to 10.3358 | |

TABLE 17

One-way analysis of variance Time required to lose 1 point on the MMSE scale (Sample Size = 21)

Table 17.1—Levene's Test for Equality of Variances

| | |
| --- | --- |
| Levene statistic | 1.77 |
| DF 1 | 1 |
| DF 2 | 19 |
| Significance level | P = 0.199 |

Table 17.2—ANOVA

| Source of variation | Sum of squares | DF | Mean square |
| --- | --- | --- | --- |
| Between groups (influence factor) | 302.7371 | 1 | 302.7371 |
| Within groups (other fluctuations) | 315.2768 | 19 | 16.5935 |
| Total | 618.0139 | 20 | |
| F-ratio | 18.244 | | |
| Significance level | P < 0.001 | | |

Table 17.3—Student-Newman-Keuls test for all pairwise comparisons

| Combined Test | n | Mean | Different (P < 0.05) from factor nr |
| --- | --- | --- | --- |
| (1) Negative | 2 | 20.2077 | −2 |
| (2) Positive | 19 | 7.2731 | −1 |

The invention claimed is:

1. A method of determining a probability value that is a diagnostic criterion associated with Alzheimer's disease in a human subject, the diagnostic criterion being derived from a cell cycle regulatory defect at G1/S phase transition and the presence of an apoE4 genotype; wherein the method comprises the steps of:
   i) obtaining a sample from the human subject;
   ii) detecting the presence of a cell cycle regulatory defect at the G1/S phase transition in at least one non-neuronal cell from the sample obtained from the human subject in step i), wherein said detecting for the presence of a cell cycle regulatory defect at the G1/S phase transition is carried out by:
      inducing cell division in the non-neuronal cell or cells from the sample from the human subject and testing the responsiveness of the cell or cells to a cell division inhibitor substance, wherein a reduced responsiveness to the cell division inhibitor substance in the cell or cells from the sample of the human subject, as compared to control cells not having a cell cycle regulatory defect at the G1/S phase transition, is an indication of the presence of a cell cycle regulatory defect at the G1/S phase transition; and
   iii) detecting the presence of the apoE4 genotype from cells of the sample of the same human subject of step i),
   wherein the result of step iii) and the result of step ii) are entered as variables into a diagnostic predictor equation in order to derive a probability value that is a diagnostic criterion associated with Alzheimer's disease;
   wherein the diagnostic predictor equation has coefficients obtained by performing steps (i)-(iii) on a population of test human subjects and combining the results obtained by performing steps (i)-(iii) on a population of test human subjects by logistic regression.

2. A method of improving the accuracy of a screen for the presence of a cell cycle regulatory defect associated with Alzheimer's disease in a human subject, wherein the method comprises the steps of:
   i) obtaining a sample from the human subject;
   ii) detecting the presence of a cell cycle regulatory defect at the G1/S phase transition in at least one non-neuronal cell from the sample obtained from the human subject in step i), wherein said detecting for the presence of a cell cycle regulatory defect at the G1/S phase transition is carried out by:
      inducing cell division in the non-neuronal cell or cells from the sample from the human subject and testing the responsiveness of the cell or cells to a cell division inhibitor substance, wherein a reduced responsiveness to the cell division inhibitor substance in the cell or cells from the sample of the human subject, as compared to control cells not having a cell cycle regulatory defect at the G1/S phase transition, is an indication of the presence of a cell cycle regulatory defect at the G1/S phase transition; and
   iii) detecting the presence of the apoE4 genotype from cells of the sample of the same human subject of step i),
   wherein the result of step iii) and the result of step ii) are entered as variables into a diagnostic predictor equation in order to derive a probability value that is improved in comparison to the result obtained in step ii),
   wherein the diagnostic predictor equation has coefficients obtained by performing steps (i)-(iii) on a population of test human subjects and combining the results obtained by performing steps (i)-(iii) on a population of test human subjects by logistic regression.

3. A method of determining the risk of developing Alzheimer's disease in a human subject, wherein the method comprises the steps of:
   i) obtaining a sample from the human subject;
   ii) detecting the presence of a cell cycle regulatory defect at the G1/S phase transition in at least one non-neuronal cell from the sample obtained from the human subject in step i), wherein said detecting for the presence of a cell cycle regulatory defect at the G1/S phase transition is carried out by:
      inducing cell division in the non-neuronal cell or cells from the sample from the human subject and testing the responsiveness of the cell or cells to a cell division inhibitor substance, wherein a reduced responsiveness to the cell division inhibitor substance in the cell or cells from the sample of the human subject, as compared to control cells not having a cell cycle regulatory defect at the G1/S phase transition, is an indication of the presence of a cell cycle regulatory defect at the G1/S phase transition; and
   iii) detecting the presence of the apoE4 genotype from cells of the sample of the same human subject of step i),
      wherein the result of step iii) and the result of in step ii), are entered as variables into a diagnostic predictor equation in order to derive a probability value for the human subject's risk of developing Alzheimer's disease,
      wherein the diagnostic predictor equation has coefficients obtained by performing steps (i)-(iii) on a population of test human subjects and combining the results obtained by performing steps (i)-(iii) on a population of test human subjects by logistic regression.

4. A method according to claim 3 wherein the human subject is asymptomatic for Alzheimer's disease, or exhibits mild cognitive impairment.

5. A method to assist with clinical diagnosis of Alzheimer's disease in a live human subject, wherein the method comprises the steps of:
   i) obtaining a sample from the live human subject;
   ii) detecting the presence of a cell cycle regulatory defect at the G1/S phase transition in at least one non-neuronal cell from the sample obtained from the live human subject in step i), wherein said detecting for the presence of a cell cycle regulatory defect at the G1/S phase transition is carried out by:
      inducing cell division in the non-neuronal cell or cells from the sample from the live human subject and testing the responsiveness of the cell or cells to a cell division inhibitor substance, wherein a reduced responsiveness to the cell division inhibitor substance in the cell or cells from the sample of the live human subject, as compared to control cells not having a cell cycle regulatory defect at the G1/S phase transition, is an indication of the presence of a cell cycle regulatory defect at the G1/S phase transition; and
   iii) detecting the presence of the apoE4 genotype from cells of the sample of the same live human subject of step i),
   wherein the result of step iii) and the result of step ii) are entered as variables into a diagnostic predictor equation in order to derive a probability value that is indicative of the subject having Alzheimer's disease,
   wherein the diagnostic predictor equation has coefficients obtained by performing steps (i)-(iii) on a population of test human subjects and combining the results obtained by performing steps (i)-(iii) on a population of test human subjects by logistic regression.

6. The method as claimed in claim 5 wherein the human subject to be tested exhibits one or more symptoms consistent with Alzheimer's disease.

7. The method according to claim 6 wherein the one or more symptoms consistent with Alzheimer's disease include cognitive decline or dementia.

8. A method for assessing the efficacy of a candidate therapy for the treatment of Alzheimer's disease in a human subject recipient of such therapy, wherein the method comprises the steps of:
   i) obtaining a sample from the human subject;
   ii) detecting the extent of a cell cycle regulatory defect at the G1/S phase transition in at least one non-neuronal cell from the sample obtained from said human subject in step i), wherein said detecting the extent of a cell cycle regulatory defect at the G1/S phase transition is carried out by:
      inducing cell division in the non-neuronal cell or cells from the sample from the human subject and testing the responsiveness of the cell or cells to a cell division inhibitor substance, wherein a reduced responsiveness to the cell division inhibitor substance in the cell or cells from the sample of the human subject, as compared to control cells not having a cell cycle regulatory defect at the G1/S phase transition, is an indication of the extent of a cell cycle regulatory defect at the G1/S phase transition; and
   iii) detecting the presence of the apoE4 genotype from cells of the sample of the same human subject of step i),
   wherein the result of step iii) and the result of step ii) are entered as variables into a diagnostic predictor equation in order to derive a probability value that is indicative of a diagnostic criterion associated with the efficacy of said candidate therapy for the treatment of Alzheimer's disease
   wherein the diagnostic predictor equation has coefficients obtained by performing steps (i)-(iii) on a population of test human subjects and combining the results obtained by performing steps (i)-(iii) on a population of test human subjects by logistic regression.

9. A method of determining a prognostic criterion that is indicative of the rate of cognitive decline due to Alzheimer's Disease in a human subject, wherein the method comprises the steps of:
   i) obtaining a sample from the human subject;
   ii) detecting the presence of or the extent of a cell cycle regulatory defect at the G1/S phase transition in at least one non-neuronal cell from the sample obtained from the human subject in step i), wherein said detecting the presence or extent of a cell cycle regulatory defect at the G1/S phase transition is carried out by:
      inducing cell division in the non-neuronal cell or cells from the sample from the human subject and testing the responsiveness of the cell or cells to a cell division inhibitor substance, wherein a reduced responsiveness to the cell division inhibitor substance in the cell or cells from the sample of the human subject, as compared to control cells not having a cell cycle regulatory defect at the G1/S phase transition, is an indication of the extent of a cell cycle regulatory defect at the G1/S phase transition; and
   iii) detecting the presence of the apoE4 genotype from cells of the sample of the same human subject of step i),
   wherein the result of step iii) and the result of step ii) are entered as variables into a diagnostic predictor equation in order to derive a probability value that is indicative of the prognostic criterion indicative of the rate of cognitive decline due to Alzheimer's disease in the human subject
   wherein the diagnostic predictor equation has coefficients obtained by performing steps (i)-(iii) on a population of test human subjects and combining the results obtained by performing steps (i)-(iii) on a population of test human subjects by logistic regression.

10. The method according to claim 1 wherein the cell division inhibitor substance is a G1 inhibitor.

11. The method according to claim 10 wherein the G1 inhibitor is rapamycin.

12. The method according to claim 1 wherein said testing of the responsiveness of the cell or cells to the cell division inhibitor substance comprises calculating the relative lengthening of the G1 phase of the cell cycle in non-neuronal cells from the sample, a reduced relative lengthening of the G1 phase in the presence of the cell division inhibitor substance in said cells, as compared to control cells not having a cell cycle regulatory defect at the G1/S phase transition.

13. The method according to claim 1 wherein said testing of the responsiveness of the cell or cells to the cell division inhibitor substance comprises assessment of cell proliferation activity, wherein increased cell proliferation activity in the presence of the cell division inhibitor substance, as compared to control cells not having a cell cycle regulatory defect at the G1/S phase transition, is taken as an indication of a cell cycle regulatory defect at the G1/S phase transition.

14. The method according to claim 13 wherein cell proliferation activity is assessed by calculating the relative lengthening of cell division time in non-neuronal cells from the sample cultured with cell division inhibitor substance, as compared to non-neuronal cells from the sample cultured without the cell division inhibitor substance.

15. The method according to claim 13 wherein cell proliferation activity is assessed by cytotoxicity assay.

16. The method according to claim 1 wherein step iii) comprises determining the number of apoE4 alleles carried by the human subject.

17. The method of claim 1 wherein step ii) comprises the steps of:
   (a) culturing at least one non-neuronal cell from the sample obtained from the human subject in the presence and absence of rapamycin,
   (b) calculating the relative lengthening of the G1 phase of the cell cycle in the non-neuronal cell or cells from the sample of the human subject cultured with rapamycin, as compared to the non-neuronal cell or cells from the sample of the human subject cultured without rapamycin, and
   (c) independently calculating the relative lengthening of cell division time of at least one non-neuronal cell from the sample from the human subject cultured with rapamycin, as compared at least one non-neuronal cell from the sample of the human subject cultured without rapamycin, wherein a combined G1 phase result from part (b) and part (c) is obtained;

wherein step iii) comprises determining the number of apoE4 alleles present in the human subject to obtain an apoE4 allele result; and wherein the result of the combined G1 phase result and apoE4 allele result are entered as variables into the diagnostic predictor equation in order to derive a probability value that is indicative of the diagnostic criterion associated with Alzheimer's Disease.

18. The method according to claim 1 wherein the non-neuronal cell or cells are lymphocytes.

* * * * *

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: PCR Primer

<400> SEQUENCE: 1
tccaaggagc tgcaggcggc gca                                                23

-continued

```
<210> SEQ ID NO 2
<211> LENGTH: 31
<212> TYPE: DNA
<213> ORGANISM: Artificial Sequence
<220> FEATURE:
<223> OTHER INFORMATION: PCR Primer

<400> SEQUENCE: 2
acagaattcg ccccggcctg gtacactgcc a                                31
```